United States Patent
Sato et al.

(10) Patent No.: US 8,927,221 B2
(45) Date of Patent: Jan. 6, 2015

(54) DIAGNOSTIC MARKER FOR KIDNEY DISEASES AND USE THEREOF

(71) Applicants: Sysmex Corporation, Kobe-shi, Hyogo (JP); Human Metabolome Technologies, Inc., Tsuruoka-shi, Yamagata (JP)

(72) Inventors: Hajime Sato, Tsuruoka (JP); Yoshiaki Ohashi, Tsuruoka (JP); Kazunori Sasaki, Tsuruoka (JP); Kouzou Suto, Kobe (JP); Yasuhiro Otomo, Kobe (JP)

(73) Assignees: Sysmex Corporation, Hyogo (JP); Human Metabolome Technologies, Inc., Yamagata (JP)

( * ) Notice: Subject to any disclaimer, the term of this patent is extended or adjusted under 35 U.S.C. 154(b) by 0 days.

(21) Appl. No.: 13/660,440

(22) Filed: Oct. 25, 2012

(65) Prior Publication Data

US 2013/0157252 A1    Jun. 20, 2013

Related U.S. Application Data

(63) Continuation of application No. PCT/JP2011/060178, filed on Apr. 26, 2011.

(30) Foreign Application Priority Data

Apr. 27, 2010 (JP) ................. 2010-102374

(51) Int. Cl.
*G01N 33/53* (2006.01)
*G01N 33/68* (2006.01)
*G01N 27/62* (2006.01)

(52) U.S. Cl.
CPC .......... *G01N 27/62* (2013.01); *G01N 2800/347* (2013.01); *G01N 33/6893* (2013.01); *G01N 33/6806* (2013.01)
USPC .......................................... 435/7.1

(58) Field of Classification Search
None
See application file for complete search history.

(56) References Cited

U.S. PATENT DOCUMENTS

| 4,957,936 A | 9/1990 | Nakamura et al. |
| 5,013,750 A | 5/1991 | Nakamura et al. |
| 2011/0246081 A1* | 10/2011 | Skolnick et al. ................ 702/20 |

FOREIGN PATENT DOCUMENTS

| JP | 2-288867 A | 11/1990 |
| JP | 2001-174459 A | 6/2001 |

OTHER PUBLICATIONS

Miasiro et al. (Euro. J. Pharmaco. 1983 vol. 87, p. 397-406; see Abstract).*
Lever M. et al., "Abnormal glycine betaine content of the blood and urine of diabetic and renal patients", Clinica Chimica Acta, *Elsevier v. Amsterdam*, NL, vol. 230, No. 1, Oct. 14, 1994, pp. 69-79.
Olivier Levillain et al., "Guanidino compound metabolism in rats subjected to 20% to 90% nephrectomy", Kidney International, vol. 47, No. 2, Feb. 1, 1995, pp. 464-472.
William H. Porter et al., "Ethylene Glycol Toxicity: The Role of Serum Glycolic Acid in Hemodialysis", Clinical Toxicology, 2001, pp. 607-615, vol. 39, No. 6.

* cited by examiner

*Primary Examiner* — Jacob Cheu
(74) *Attorney, Agent, or Firm* — Sughrue Mion, PLLC

(57) ABSTRACT

The present invention relates to novel diagnostic markers for kidney disease and the use thereof.

4 Claims, 19 Drawing Sheets

A

Healthy    Diabetes  Early    Overt

B

Healthy    Diabetes  Early    Overt

C

Healthy    Diabetes  Early    Overt

D

Healthy    Diabetes  Early    Overt

DIAGNOSTIC MARKER FOR KIDNEY DISEASES AND USE THEREOF

CROSS-REFERENCE TO RELATED APPLICATION

This application is a continuation of International Application PCT/JP2011/060178 filed on Apr. 26, 2011, which claims benefit of Japanese patent application JP 2010-102374 filed on Apr. 27, 2010, both of which are incorporated herein by reference in their entireties.

BACKGROUND OF THE INVENTION

The present invention relates to a diagnostic marker for kidney disease and a computer program for diagnosis of kidney disease using the marker.

Kidney diseases are caused by pathological lesions in kidney tissues. Kidney diseases mainly include 1) glomerulonephritis due to pathological lesions in glomerulus which is responsible for blood filtration, 2) tubulointerstitial nephritis due to pathological lesions in renal tubules which is responsible for resorption of water or electrolytes from primitive urine, 3) arteriolosclerosis due to renovascular pathological lesions and the like.

When a patient develops renal failure from kidney disease, it is difficult to restore and maintain renal functions even after initiation of therapeutic treatments. In this case, the patient needs to undergo dialysis treatment. The number of patients who require dialysis treatment is increasing recently and it causes a problem of growth in medical costs.

Thus, it is important to identify kidney disease patients at early stages by accurate diagnoses.

In the current kidney disease diagnoses, renal function is evaluated by measurement of glomerular filtration rate (GFR).

Kidney disease diagnostic markers are also used such as urine albumin, type IV collagen, transferrin, IgG, laminin, fibronectin, α-1 microglobulin, β-2 microglobulin, cystatin C, N-acetyl-β-D-glucosaminidase (NAG), L-fatty acid binding protein (L-FABP), glycocyamidine and derivatives thereof and the like (see Japanese Unexamined Patent Publication Nos. HEI 2 (1990)-288867 and 2001-174459).

However, in order to provide further highly accurate diagnoses of kidney diseases, measurements of GFR and use of the above diagnostic markers are not sufficient. Therefore, there is a need for development of novel markers useful for diagnoses of kidney disease.

SUMMARY OF THE INVENTION

An object of the present invention is to provide novel diagnostic markers for kidney disease. Another object of the present invention is to provide a computer program for diagnosis of kidney disease using the diagnostic markers for kidney disease.

The present inventors analyzed the specimens obtained from healthy subjects and kidney disease patients by capillary electrophoresis mass spectrometry (CE-MS) and, as a result, found new diagnostic markers for kidney disease, thereby completing the present invention.

Namely, according to the present invention, a diagnostic marker for kidney disease is provided which is at least one selected from:
glycolic acid;
$N^5$-[(dimethylamino)iminomethyl]-ornithine;
5-oxo-2-tetrahydrofuran carboxylic acid;
a combination consisting of trimethylglycine and any one substance selected from glycolic acid, $N^5$-[(dimethylamino)iminomethyl]-ornithine, guanidinoacetic acid, 4-guanidinobutyric acid, $N^6$-acetyllysine, $N^1$-acetylhistidine and histidine;
a combination consisting of glycolic acid and any one substance selected from $N^5$-[(dimethylamino)iminomethyl]-ornithine, cytidine, valine, kynurenine, 2-oxoglutaric acid, glycocyamidine and choline;
a combination consisting of cystine and any one substance selected from $N^1$-acetylhistidine, histidine, glycine, tryptophan and methionine; and
a combination consisting of tryptophan and ornithine.

According to the present invention, a computer program is also provided which is configured to cause a computer to operate the steps of:
obtaining a concentration of the above diagnostic marker in urine and/or plasma obtained from a subject suspected to have kidney disease;
determining whether or not the subject has kidney disease based on the obtained concentration; and
delivering the result of determination.

According to the present invention, diagnostic markers for kidney disease useful for diagnoses with increased accuracy can be provided. The diagnostic markers for kidney disease of the present invention allow not only diagnosis of a subject on kidney disease but also, in case the subject has received treatment for kidney disease, evaluation of an extent of improvement in symptoms and efficacy of the treatment.

Further, according to the present invention, the computer program can be provided for diagnoses of kidney disease using the above diagnostic markers for kidney disease.

BRIEF DESCRIPTION OF THE DRAWINGS

FIGS. 1A and 1C show the patterns in which the concentration and the like continuously increase or decrease from the healthy stage to the overt nephropathy stage and FIGS. 1B and 1D show the patterns in which the concentration and the like continuously increase or decrease from the healthy stage to the early nephropathy stage and do not show any change from the early nephropathy stage to the overt nephropathy stage;

FIG. 7A shows the quantitative values in urine, FIG. 7B shows the quantitative values in plasma and FIG. 7C shows the ratios between the quantitative values in urine and plasma;

DETAILED DESCRIPTION OF THE INVENTION

Figure 1:
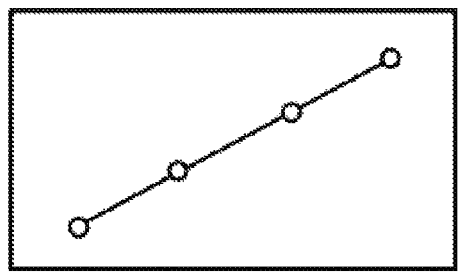
FIG. 1 shows graphs representing variation patterns of the concentration or concentration ratio of the diagnostic markers for kidney disease of the present invention depending on respective pathological conditions of kidney diseases.
Figure 1:
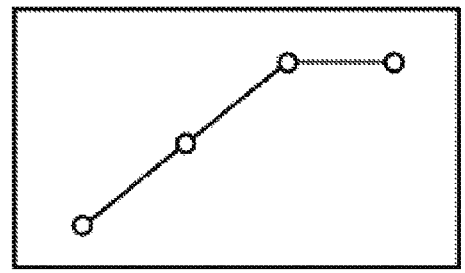
Figure 1:
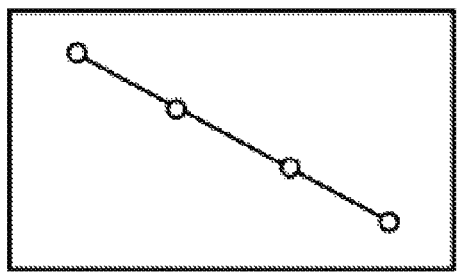
Figure 1:
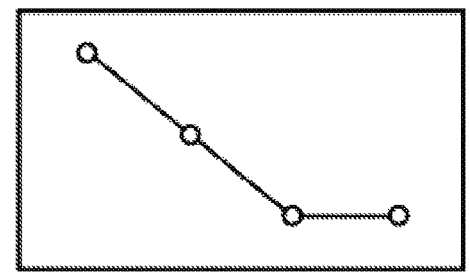

The following formulae represent the names and chemical structures of the substances used as the diagnostic markers for kidney disease of the present invention. The diagnostic markers for kidney disease of the present invention comprise one substance or a combination of two substances shown below.

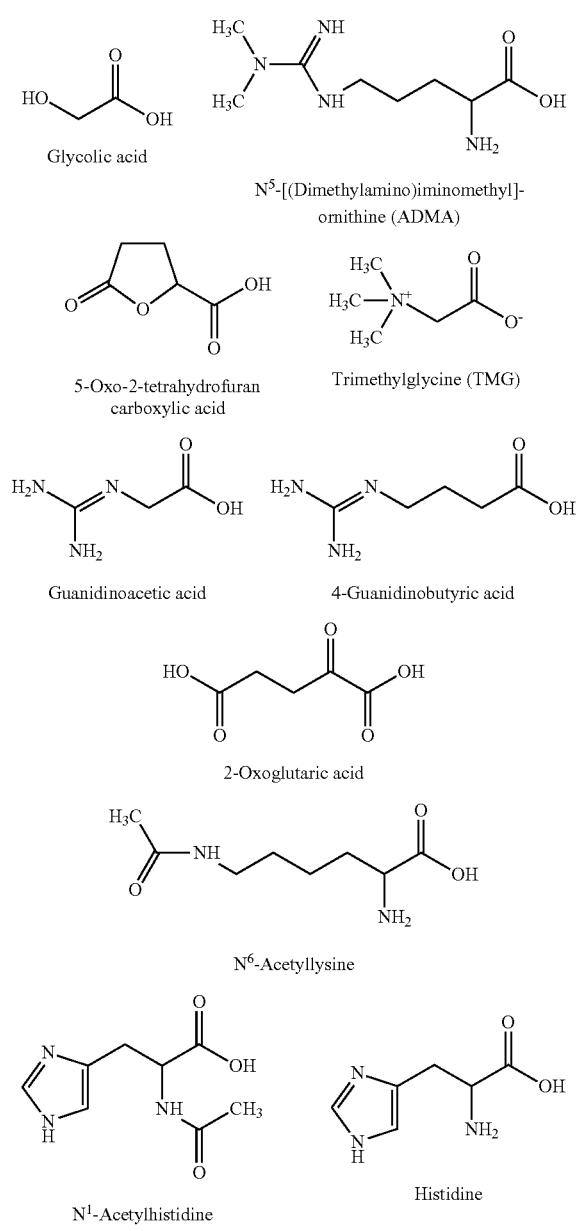

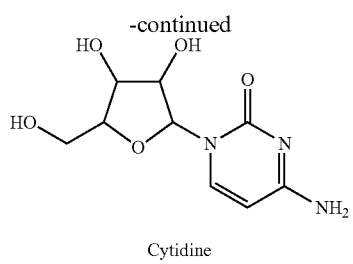
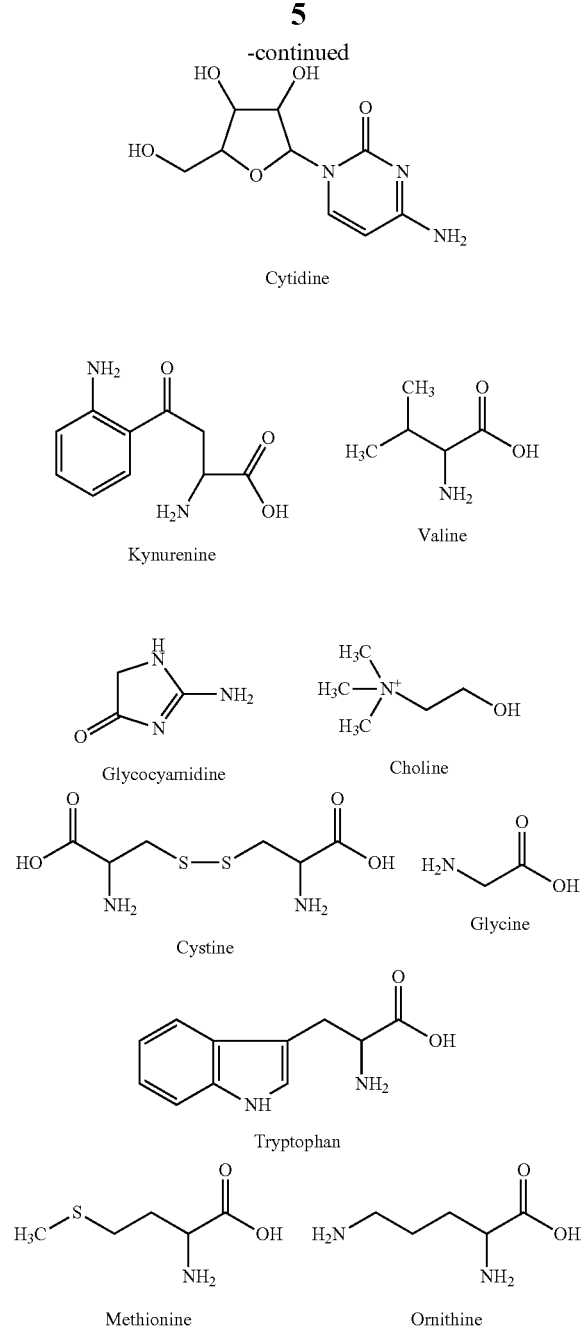

The diagnostic marker for kidney disease consisting of a combination of two substances includes the following combinations 1 to 4. The combinations 1 to 4 are specifically represented in Tables 1 to 4. Namely, the diagnostic marker for kidney disease of the present invention consisting of a combination of two substances is selected from the combinations of the substance A and the substance B shown in these Tables.

(Combination 1)

A combination of the substance A which is trimethylglycine (TMG) and the substance B which is any one substance selected from glycolic acid, $N^5$-[(dimethylamino)iminomethyl]-ornithine (ADMA), guanidinoacetic acid, 4-guanidinobutyric acid, $N^6$-acetyllysine, $N^1$-acetylhistidine and histidine.

TABLE 1

| Substance A | Substance B |
|---|---|
| TMG | Glycolic acid |
| TMG | ADMA |
| TMG | Guanidinoacetic acid |
| TMG | 4-Guanidinobutyric acid |
| TMG | $N^6$-Acetyllysine |
| TMG | $N^1$-Acetylhistidine |
| TMG | Histidine |

(Combination 2)

A combination of the substance A which is glycolic acid and the substance B which is any one substance selected from ADMA, cytidine, valine, kynurenine, 2-oxoglutaric acid, glycocyamidine and choline.

TABLE 2

| Substance A | Substance B |
|---|---|
| Glycolic acid | ADMA |
| Glycolic acid | Cytidine |
| Glycolic acid | Valine |
| Glycolic acid | Kynurenine |
| Glycolic acid | 2-Oxoglutaric acid |
| Glycolic acid | Glycocyamidine |
| Glycolic acid | Choline |

(Combination 3)

A combination of the substance A which is cystine and the substance B which is any one substance selected from $N^1$-acetylhistidine, histidine, glycine, tryptophan and methionine.

TABLE 3

| Substance A | Substance B |
|---|---|
| Cystine | $N^1$-acetylhistidine |
| Cystine | Histidine |
| Cystine | Glycine |
| Cystine | Tryptophan |
| Cystine | Methionine |

(Combination 4)

A combination of the substance A which is tryptophan and the substance B which is ornithine.

TABLE 4

| Substance A | Substance B |
|---|---|
| Tryptophan | Ornithine |

In the present invention, the kidney disease may be a disease resulting from pathological lesions in renal tissues without particular limitation. The kidney disease may include, for example, diabetic nephropathy, glomerulonephritis, tubulointerstitial nephritis and the like.

Among the above kidney diseases, the diagnostic marker for kidney disease of the present invention may be suitably used as the diagnostic marker for diabetic nephropathy accompanying diabetes.

It is possible to use the diagnostic markers for kidney disease of the present invention for carrying out diagnoses of kidney disease. The diagnosis method may be the one in which the diagnostic marker for kidney disease is measured in urine and/or plasma obtained from a subject suspected to have kidney disease, without particular limitation. For example, diagnosis of kidney disease can be carried out based on the result of measurement of the concentration of the diagnostic marker for kidney disease in urine and/or plasma obtained from a subject suspected to have kidney disease. "Diagnosis of kidney disease" includes definitive diagnosis of kidney disease, a screening test for kidney disease and an evaluation of treatment efficacy of kidney disease, among which a screening test for kidney disease is preferable.

Urine obtained from a subject may be any urine regardless of the physical condition of the subject, timing of meals, medication which the subject receives, if any, or the time of sampling, without limitation. However, it is preferably morning urine (first urine). Plasma obtained from a subject may also be any plasma obtained from blood sampled from a subject regardless of the physical condition of the subject, timing of meals, medication which the subject receives, if any, or the time of sampling, without limitation.

Specific examples of the diagnosis method of kidney disease using the present marker are described hereinbelow.

Embodiment 1 and Embodiment 2 described hereinbelow are the diagnosis methods for kidney disease in which the diagnostic markers for kidney disease consisting of a single substance are used.

Embodiment 1

(1) Measure the concentration of the marker in urine or plasma obtained from a subject suspected to have kidney disease;
(2) Compare the measured concentration of the marker with a threshold; and
(3) Based on the result of comparison, determine whether or not the subject has kidney disease.

Embodiment 2

(1) Measure the concentration of the marker in urine and plasma obtained from a subject suspected to have kidney disease;
(2) Obtain a value relating to the ratio between the concentration of the marker in urine and the concentration in plasma;
(3) Compare the obtained value relating to the ratio between the concentration of the marker in urine and the concentration in plasma with a threshold;
(4) Based on the result of comparison, determine whether or not the subject has kidney disease.

In Embodiment 2, the value relating to the ratio between the concentration of the marker in urine and the concentration in plasma may include the values of "the concentration in plasma/the concentration in urine" and "the concentration in urine/the concentration in plasma"

The diagnostic marker for kidney disease used for the above Embodiment 1 and Embodiment 2 is suitably any of glycolic acid, ADMA and 5-oxo-2-tetrahydrofuran carboxylic acid.

The following Embodiment 3 is the diagnosis method of kidney disease in which the diagnostic marker for kidney disease consisting of a combination of two substances is used.

Embodiment 3

(1) Measure the concentrations of two substances in urine and/or plasma obtained from a subject suspected to have kidney disease;
(2) Obtain a value relating to the ratio between the measured concentrations of two substances;
(3) Compare the obtained value relating to the concentration ratio between two substances with a threshold; and
(4) Based on the result of comparison, determine whether or not the subject has kidney disease.

In Embodiment 3, the value relating to the concentration ratio between two substances may include, provided that two substances constituting the marker are the substances A and B, respectively, the values "A (plasma)/B (plasma)", "A (plasma)/B (urine)", "A (urine)/B (plasma)", "A (urine)/B (urine)", "B (plasma)/A (plasma)", "B (plasma)/A (urine)", "B (urine)/A (plasma)" and "B (urine)/A (urine)"

"A (plasma)" and "A (urine)" represent the concentrations of the substance A in plasma and urine, respectively, and "B (plasma)" and "B (urine)" represent the concentrations of the substance B in plasma and urine, respectively.

The diagnostic marker for kidney disease used for the above Embodiment 3 is suitably the marker selected from the above combinations 1 to 4.

The threshold may be determined as follows, for example. First, urine and/or plasma is taken from a subject who is confirmed to have no kidney disease according to the conventional method (i.e., a healthy subject). Next, the urine and/or plasma is measured for the concentration of the diagnostic marker for kidney disease of the present invention and the value of the concentration and the value relating to the concentration ratio are obtained. The obtained result is then used as a predetermined threshold. The threshold determined as above allows determination on whether or not a subject undergoing diagnosis using the diagnostic marker for kidney disease of the present invention is healthy or has kidney disease.

Alternatively, the threshold may be determined by using urine and/or plasma obtained from a subject suffering from stage I or II diabetic nephropathy, instead of urine and/or plasma obtained from a healthy subject. In this case, the obtained threshold allows determination on whether a subject undergoing diagnosis using the diagnostic marker for kidney disease of the present invention has stage I or II diabetic nephropathy or severer kidney disease.

Upon determination of the threshold, samples are preferably obtained from more than one healthy subject and/or subject having stage I or II diabetic nephropathy.

The method for measuring the concentration of the diagnostic marker for kidney disease in urine and plasma may be appropriately selected according to physical or chemical properties of the marker substance without particular limitation.

For example, a sample to be measured may be prepared from urine or plasma obtained from a subject suspected to have kidney disease. The marker contained in the sample may be then isolated by high performance liquid chromatography (HPLC), gas chromatography (GC), capillary electrophoresis (CE) and the like. The isolated marker is then subjected to a measurement system such as UV detection, fluorescence detection, mass spectrometry (MS) and the like to measure the concentration of the marker in urine or plasma.

Alternatively, the concentration of the marker in urine or plasma can be measured by bringing the marker contained in urine or plasma obtained from the subject into contact with an enzyme which can react with the marker as a substrate and subjecting the enzyme reaction product to a measurement system such as a method using redox electrodes, colorimetric method and the like.

FIG. 1 exemplifies variation patterns of the concentration or concentration ratio of the diagnostic markers for kidney disease of the present invention in respective pathological conditions of kidney diseases. In this figure, "Healthy" represents healthy subjects, "Diabetes" represents patients with stage I diabetic nephropathy (initial stage of nephropathy), "Early" represents patients with stage II diabetic nephropathy (early stage of nephropathy), and "Overt" represents patients with stages III and IV diabetic nephropathy (overt nephropathy stage).

FIG. 1A shows the variation pattern with the tendency that the concentration or concentration ratio of the marker increases with the progress of the stage of kidney disease from "Healthy" to "Overt".

FIG. 1B shows the variation pattern with the tendency that the concentration or concentration ratio of the marker increases from "Healthy" to "Early", while it is almost constant from "Early" to "Overt".

FIG. 1C shows the variation pattern with the tendency that the concentration or concentration ratio of the marker decreases with the progress of the stage of kidney disease from "Healthy" to "Overt".

FIG. 1D shows the variation pattern with the tendency that the concentration or concentration ratio of the marker decreases from "Healthy" to "Early", while it is almost constant from "Early" to "Overt".

As described above, the concentration or concentration ratio of the diagnostic marker for kidney disease of the present invention follows the variation patterns such that it increases or decreases from "Healthy" to "Early". Because of this, a threshold determined so as to be the concentration or concentration ratio of the diagnostic marker for kidney disease that allows the discrimination of "Early" allows diagnosis of kidney disease.

When glycolic acid is used as the diagnostic marker for kidney disease, the diagnosis method preferably follows "Embodiment 1" in which the concentration in urine is utilized. In this case, the concentration of glycolic acid in urine follows the variation pattern in which it decreases from "Healthy" to "Early" as shown in FIG. 1C.

Thus, when the value of the concentration of glycolic acid in urine obtained from a subject is lower than a predetermined threshold, it is diagnosed that the subject has kidney disease.

When 5-oxo-2-tetrahydrofuran carboxylic acid is used as the diagnostic marker for kidney disease, the diagnosis method preferably follows "Embodiment 1" in which the concentration in urine is utilized. In this case, the concentration of 5-oxo-2-tetrahydrofuran carboxylic acid in urine follows the variation pattern in which it decreases from "Healthy" to "Early" as shown in FIG. 1C.

Thus, when value of the concentration of 5-oxo-2-tetrahydrofuran carboxylic acid in urine obtained from a subject is lower than a predetermined threshold, it is diagnosed that the subject has kidney disease.

When $N^5$-[(dimethylamino)iminomethyl]-ornithine (ADMA) is used as the diagnostic marker for kidney disease, the diagnosis method preferably follows "Embodiment 1" in which the concentration in urine is utilized or "Embodiment 2" in which the concentrations in urine and plasma are used.

In the case of Embodiment 1, the concentration of ADMA in urine follows the variation pattern in which it decreases from "Healthy" to "Early" as shown in FIG. 1C.

Thus, when the value of the concentration of ADMA in urine obtained from a subject is lower than a predetermined threshold, it is diagnosed that the subject has kidney disease.

In the case of Embodiment 2, the value of "the concentration of ADMA in plasma/the concentration of ADMA in urine" follows the variation pattern in which it increases from "Healthy" to "Early".

Thus, when the value of "the concentration of ADMA in plasma/the concentration of ADMA in urine" is higher than a predetermined threshold, it is diagnosed that the subject has kidney disease.

When the diagnostic marker for kidney disease shown in "Combination 1" described above is used in the diagnosis method of "Embodiment 3", the concentration ratio between two substances is preferably the ratio between the concentration of trimethylglycine in urine and the concentration of the substance B shown in Table 1 in urine.

When the diagnostic marker for kidney disease shown in "Combination 2" described above is used in the diagnosis method of "Embodiment 3", the value relating to the concentration ratio between two substances is preferably the ratio between the concentration of glycolic acid in urine and the concentration of the substance B shown in Table 2 in plasma or urine.

Particularly, when the substance B is ADMA, kynurenine, 2-oxoglutaric acid or choline, the value relating to the concentration ratio between two substances is more preferably the ratio between the concentration of glycolic acid in urine and the concentration of the substance B in plasma. When the substance B is valine, cytidine or glycocyamidine, the value relating to the concentration ratio between two markers is more preferably the ratio between the concentration of glycolic acid in urine and the concentration of the substance B in urine.

When the diagnostic marker for kidney disease shown in "Combination 3" described above is used in the diagnosis method of "Embodiment 3", the value relating to the concentration ratio between two substances is preferably the ratio between the concentration of cystine in urine and the concentration of the substance B shown in Table 3 in urine.

When the diagnostic marker for kidney disease shown in "Combination 4" described above is used in the diagnosis method of "Embodiment 3", the value relating to the concentration ratio between two substances is preferably the ratio between the concentration of tryptophan in plasma and the concentration of ornithine in plasma.

The computer program of the present invention is described hereinbelow.

The computer program of the present invention is the one which is configured to cause a computer to operate the diagnosis method using the diagnostic marker for kidney disease of the present invention, preferably the diagnosis method of kidney disease according to the above Embodiments 1 to 3.

The present computer program can cause a computer to operate the steps of:

obtaining a concentration of the diagnostic marker for kidney disease of the present invention in urine and/or plasma obtained from a subject suspected to have kidney disease (hereinafter also referred to as "obtaining step");

determining whether or not the subject has kidney disease based on the obtained concentration (hereinafter also referred to as "determining step"); and delivering the result of determination.

In the preferred embodiment of the present invention, the computer program causes a computer to further operate the step of comparing the value of the concentration of the marker obtained in the obtaining step with a threshold. In this embodiment, the obtaining step is the step of obtaining the value of the concentration of at least one marker selected from glycolic acid, $N^5$-[(dimethylamino)iminomethyl]-ornithine and 5-oxo-2-tetrahydrofuran carboxylic acid in urine or plasma obtained from a subject suspected to have kidney disease and the determining step is the step of determining whether or not the subject has kidney disease based on the comparison result obtained in the comparing step. Accordingly, the present computer program can be configured to cause a computer to operate the diagnosis method according to Embodiment 1 described above.

In another preferable embodiment of the present invention, the computer program causes a computer to further operate the steps of calculating a value relating to the ratio between the concentrations of the marker in urine and plasma from the values of the concentrations of the marker in urine and plasma obtained in the obtaining step, and comparing the calculated value relating to the ratio between the concentrations of the marker in urine and plasma with a threshold. In this embodiment, the obtaining step is the step of obtaining the value of the concentration of at least one substance selected from glycolic acid, $N^5$-[dimethylamino)iminomethyl]-ornithine and 5-oxo-2-tetrahydrofuran carboxylic acid in urine and plasma obtained from a subject suspected to have kidney disease and the determining step is the step of determining whether or not the subject has kidney disease based on the comparison result obtained in the comparing step. Accordingly, the present computer program can be configured to cause a computer to operate the diagnosis method according to Embodiment 2 described above.

In another preferable embodiment of the present invention, the computer program causes a computer to further operate the steps of calculating a value relating to the ratio between the concentrations of one substance and the other substance in the diagnostic marker for kidney disease which consists of a combination of two substances from the concentrations of the two substances in urine and/or plasma obtained in the obtaining step, and comparing the calculated value relating to the ratio between the concentrations of two substances with a threshold. In this embodiment, the obtaining step is the step of obtaining the value of the concentration of at least one marker selected from the diagnostic markers for kidney disease consisting of a combination of two substances in urine and plasma obtained from a subject suspected to have kidney disease and the determining step is the step of determining whether or not the subject has the kidney disease based on the comparison result obtained in the comparing step. Accordingly, the present computer program can be configured to cause a computer to operate the diagnosis method according to Embodiment 3 described above.

In a more preferable embodiment, the combination of two substances in urine and/or plasma is the combination of trimethylglycine with $N^5$-[(dimethylamino)iminomethyl]-ornithine or guanidinoacetic acid.

The scope of the present invention also encompasses a computer readable memory medium storing the computer program.

Figure 28:
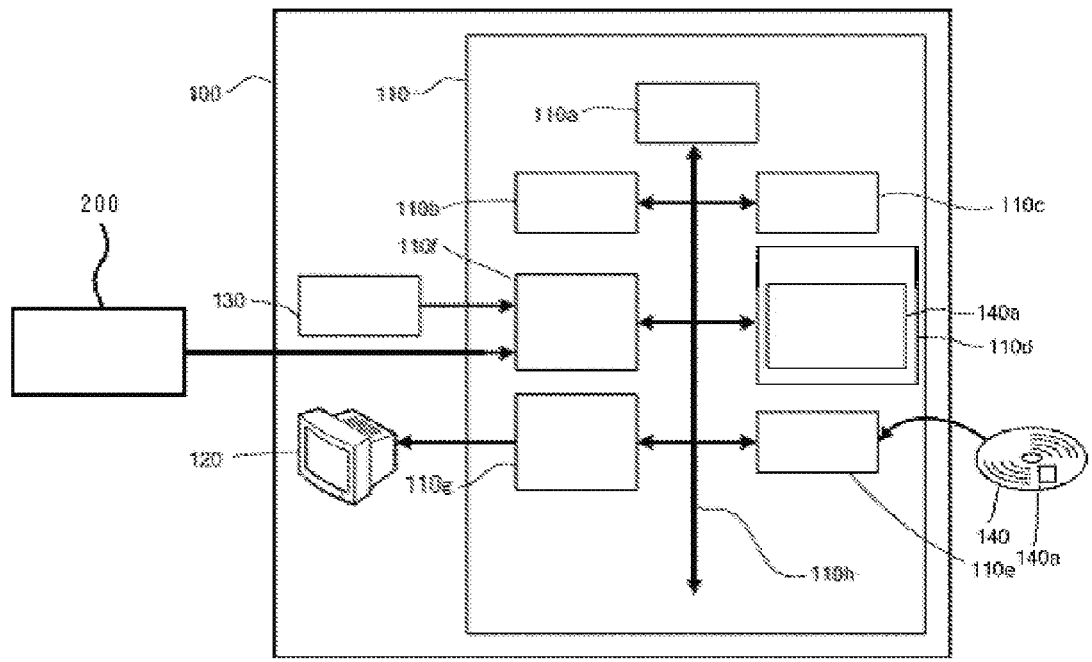
FIG. 28 is a block diagram of a computer system for executing diagnosis of kidney disease.

An example of a system of the computer in which the computer program of the present invention is executed is shown in FIG. 28.

A computer 100 is mainly constructed from a main unit 110, a display unit 120 and an input device 130. In the main unit 110, a CPU 110a, ROM 110b, RAM 110c, a hard disk 110d, a read-out system 110e, an input-output interface 110f and an image output interface 110g are connected via a bus 110h so as to be able to communicate each other.

The CPU 110a can execute the computer program stored in ROM 110b and the computer program loaded with RAM 110c. ROM 110b is made up with mask ROM, PROM, EPROM, EEPROM or the like and stores the computer program executed by the CPU 110a and data used for the execution.

RAM 110c is made up with SRAM, DRAM or the like. RAM 110c is used for readout of the computer programs stored in ROM 110b and the hard disk 110d. RAM 110c is also utilized as a work area when the CPU 110a executes these computer programs.

Various computer programs to be executed by CPU 110a such as an operating system and application system program and data necessary for execution of the computer programs are installed on the hard disk 110d. A computer program 140a which causes the computer 100 to operate the diagnosis method of kidney disease according to Embodiments 1 to 3, described herein below, and a threshold used in Embodiments 1 to 3 are also installed on the hard disk 110d.

The read-out system 110e is made up with a flexible disk drive, a CD-ROM drive or a DVD-ROM drive and the like and can readout the computer program or data stored on a portable memory medium 140.

The portable memory medium 140 is a memory medium well known per se in the art such as a flexible disk, a CD-ROM, a DVD-ROM and the like. The portable memory medium 140 stores the computer program 140a relating to the computational determination on whether or not a subject has kidney disease so as to be readout by the computer. The CPU 110a reads out the computer program 140a from the portable memory medium 140 and can install it on the hard disk 110d.

An operation system providing a graphical user interface environment such as Windows® produced and marketed by Microsoft Corporation (U.S.A.) is installed on the hard disk 110d.

In the description hereinbelow, the computer program 140a relating to the determination of kidney disease operates on the operating system.

The input-output interface 110f is made up with a serial interface such as USB, IEEE1394, RS-232C; a parallel interface such as SCSI, IDE, IEEE1284; or an analog interface formed by a D/A converter, an A/D converter or the like. The input-output interface 110f is connected to the input device 130 formed by a keyboard and a mouse. A user can input the concentration data of the diagnostic marker for kidney disease in urine and plasma obtained from a subject into the computer main unit 110 by means of the input device 130. The input-output interface 110f may be connected to a measurement apparatus 200 which can measure the concentration of the diagnostic marker for kidney disease in urine and plasma obtained from a subject. In this case, the concentration data of the diagnostic marker for kidney disease can be entered from the measurement apparatus 200 into the computer main unit 110.

The image output interface 110h is connected to the display unit 120 made up with a LCD or CRT and sends an image signal to the display unit 120 according to an image data provided by the CPU 110a. The display unit 120 outputs the image data according to the input image signal. The display unit 120 also outputs the determination result provided by the CPU 110a described hereinbelow.

The process steps executed by the computer in accordance with the present computer program are described in details by referring to the figures.

Figure 29:
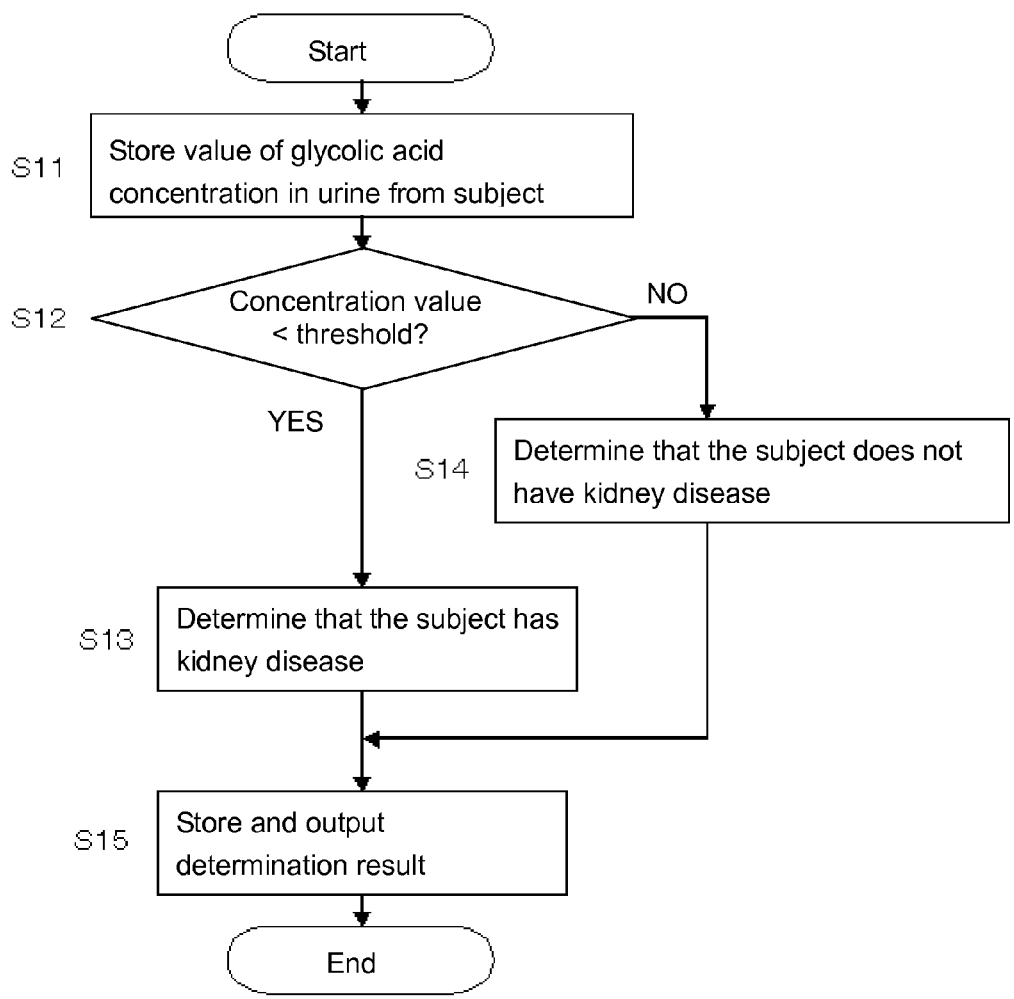
FIG. 29 is a flow chart executed by a CPU when a diagnosis method of kidney disease of Embodiment 1 is carried out by a computer.

FIG. 29 shows a flow chart executed by the CPU 110a when the diagnosis method of kidney disease of Embodiment 1 is carried out by the computer 100.

When a user enters a value of the concentration of glycolic acid in urine obtained from a subject via the input device 130, the CPU 110a stores the value of the concentration of glycolic acid via the input-output interface 110f on RAM 110c and the hard disk 110d (Step S11).

The CPU 110a retrieves a threshold (=28.4) which has been preliminarily stored on the hard disk 110d and compares it with the value of the concentration of glycolic acid (Step S12).

The CPU 110a determines that the subject has kidney disease when the value of the concentration of glycolic acid is lower than the threshold (Step S13). The CPU 110a determines that the subject does not have kidney disease when the value of the concentration of glycolic acid is not lower than the threshold (Step S14).

The CPU 110a stores the determination result on the hard disk 110d and also outputs the results on the display unit 120 via the image output interface 110g (Step S15).

In Embodiment 1 shown in FIG. 29, glycolic acid is used as the diagnostic marker for kidney disease as described above. However, it does not limit the present invention. For example, the diagnostic marker for kidney disease may be 5-oxo-2-tetrahydrofuran carboxylic acid and/or ADMA.

Figure 30:
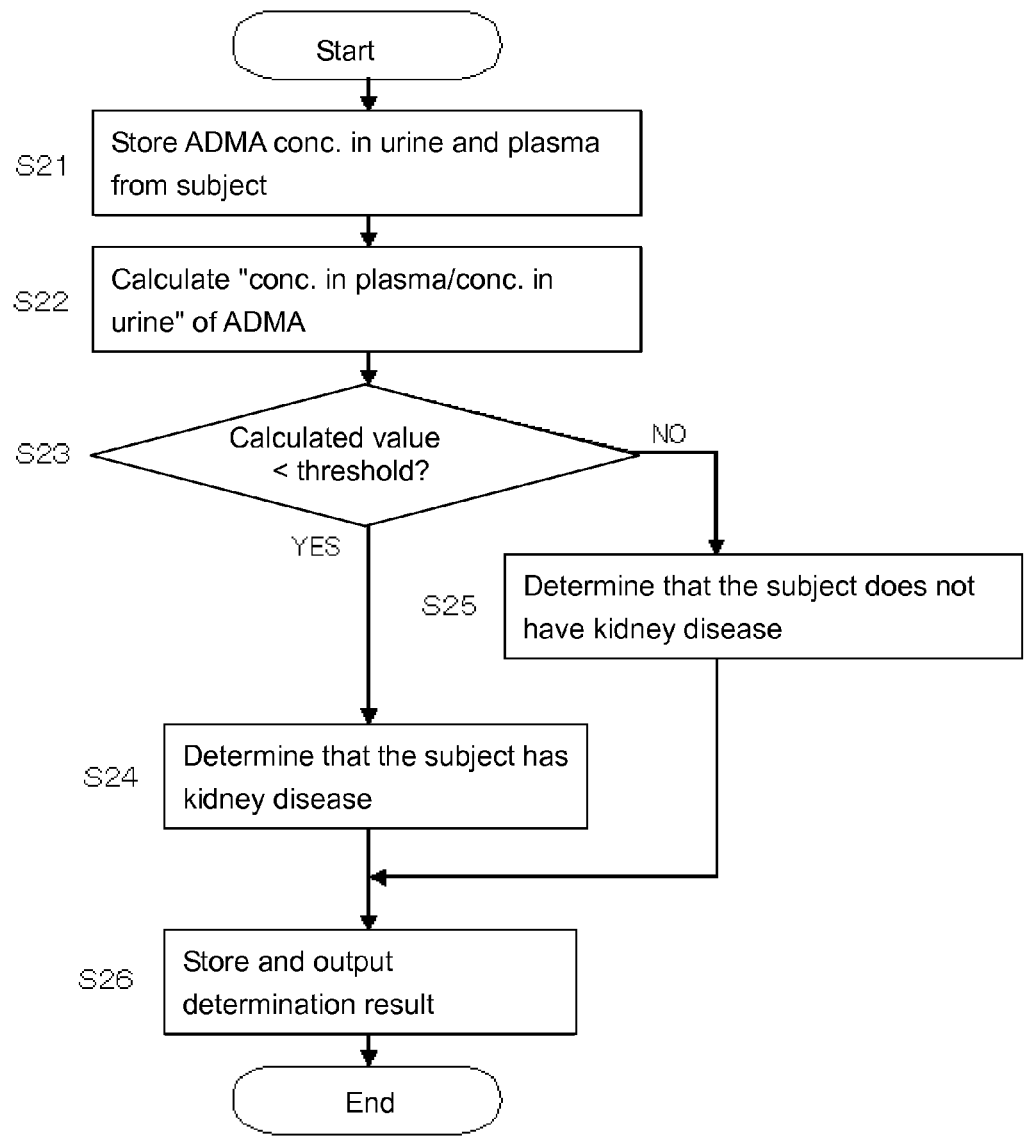
FIG. 30 is a flow chart executed by a CPU when a diagnosis method of kidney disease of Embodiment 2 is carried out by a computer.

FIG. 30 shows a flow chart executed by CPU 110a when the diagnosis method of kidney disease of Embodiment 2 is carried out by the computer 100.

When a user enters values of the concentration of ADMA in urine and plasma obtained from a subject via the input device 130, the CPU 110a stores the values of the concentration of ADMA on RAM 110c and the hard disk 110d (Step S21).

The CPU 110a reads out the values of the concentration of ADMA in urine and plasma stored on RAM 110c, calculates the value of "the concentration in plasma/the concentration in urine" of ADMA (Step S22) and stores it on RAM 110c.

The CPU 110a retrieves a threshold (=0.094) which has been preliminarily stored on the hard disk 110d and compares it with the value of "the concentration in plasma/the concentration in urine" of ADMA (Step S23).

The CPU 110a determines that the subject has kidney disease when the value of "the concentration in plasma/the concentration in urine" of ADMA is higher than the threshold (Step S24). The CPU 110a determines that the subject does not have kidney disease when the value of "the concentration in plasma/the concentration in urine" of ADMA is not higher than the threshold (Step S25).

The CPU 110a stores the determination result on the hard disk 110d and also outputs the results on the display unit 120 via the image output interface 110g (Step S26).

Figure 31:
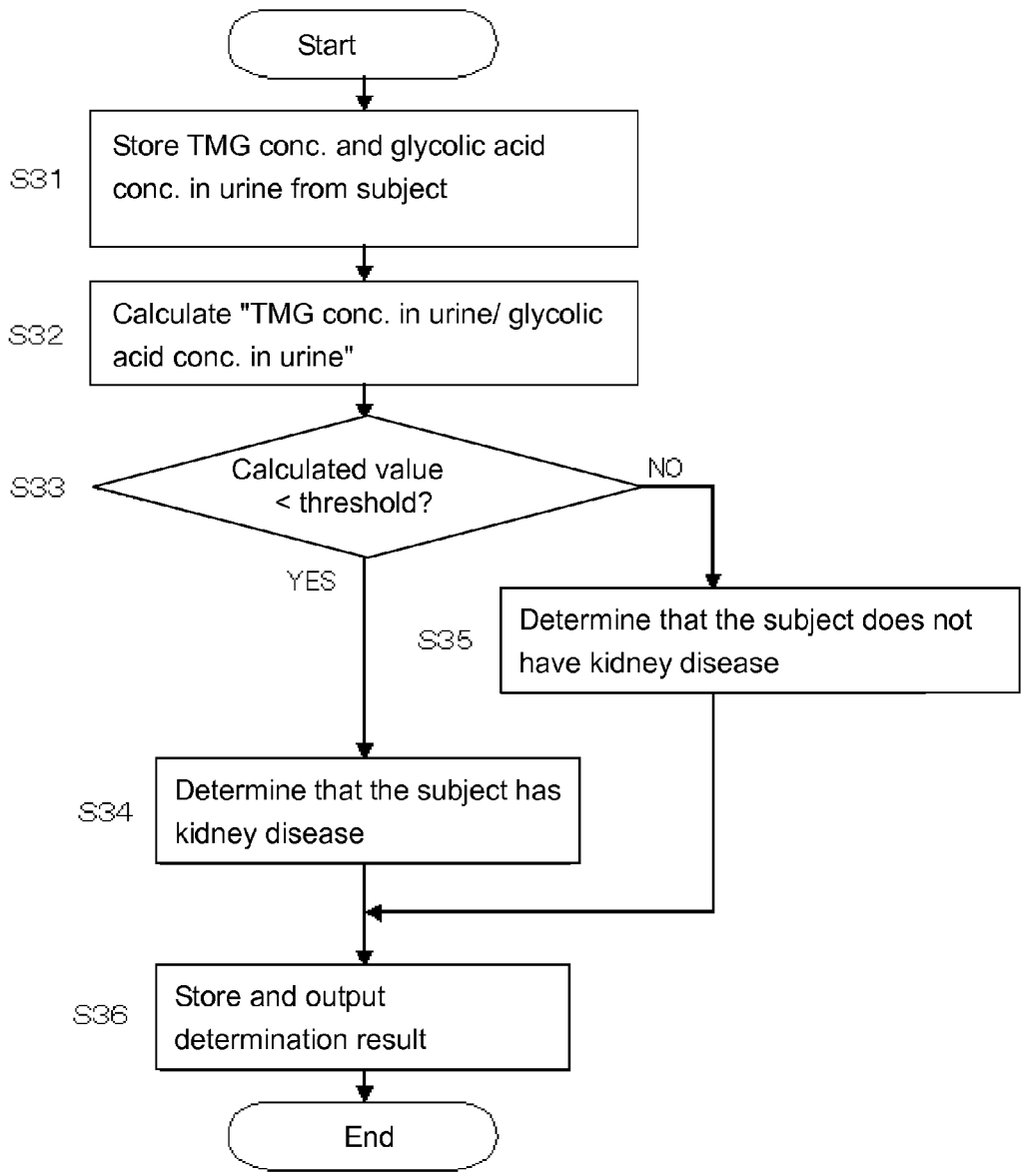
FIG. 31 is a flow chart executed by a CPU when a diagnosis method of kidney disease of Embodiment 3 is carried out by a computer.

FIG. 31 shows a flow chart executed by CPU 110a when the diagnosis method of kidney disease of Embodiment 3 is carried out by the computer 100.

When a user enters values of the concentrations of TMG and glycolic acid in urine obtained from a subject via the input device 130, the CPU 110a stores the values of the concentrations on RAM 110c and the hard disk 110d via the input-output interface 110f (Step S31).

The CPU 110a calculates the value of "the concentration of TMG in urine/the concentration of glycolic acid in urine" from the values of the concentrations of TMG and glycolic acid in urine (Step S32).

The CPU 110a retrieves a threshold (=0.64) which has been preliminarily stored on the hard disk 110d and compares it with the calculated value of "the concentration of TMG in urine/the concentration of glycolic acid in urine" (Step S33).

The CPU 110a determines that the subject has kidney disease when the value of "the concentration of TMG in urine/the concentration of glycolic acid in urine" is higher than the threshold (Step S34). The CPU 110a determines that the subject does not have kidney disease when the value of "the concentration of TMG in urine/the concentration of glycolic acid in urine" is not higher than the threshold (Step S35).

The CPU 110a stores the determination result on the hard disk 110d and also outputs the results on the display unit 120 via the image output interface 110g (Step S36).

In Embodiment 3 shown in FIG. 31, the combination of TMG and glycolic acid is used as the diagnostic marker for kidney disease as described above. However, it does not limit the present invention. Namely, the diagnostic marker for kidney disease may be the diagnostic marker for kidney disease of Combinations 1 to 4 shown in Tables 1 to 4. The ratio between TMG and glycolic acid in urine (the value of "the concentration of TMG in urine/the concentration of glycolic acid in urine") is used as the value relating to the concentration ratio in this Embodiment. However, it does not limit the present invention. The value relating to the concentration ratio may be appropriately selected according to the combination of substances used as the diagnostic marker for kidney disease. More specifically, it can be the value relating to the concentration ratio shown in Tables 7 to 10 described hereinbelow in Example 2 according to the diagnostic marker for kidney disease used.

In the above embodiments, the concentration of the marker is entered by a user via the input device 130. However, it does not limit the present invention. For example, the concentration of the marker may be entered from the measurement apparatus 200 connected via the input-output interface 110f. The concentration of the marker measured on the measurement apparatus 200 may be stored on the portable memory medium 140 and be readout by the read-out system 110e from the portable memory medium 140.

The present invention is now further described by way of Examples which do not limit the present invention.

Example 1

A metabolome analysis was carried out as follows.
(1) Samples

Specimens of plasma and morning urine (taken on the same day) were taken from 20 healthy subjects and 40 patients categorized as follows (total: 60 subjects).

Namely, the patients included the groups of diabetes patients (19 patients), stage II diabetic nephropathy patients (early nephropathy; 12 patients), stages III and IV diabetic nephropathy patients (overt nephropathy; 7 patients) and chronic kidney disease patients (CKD; 2 patients).

Chronic kidney disease patients mean the patients having non-diabetic nephropathy. Namely, it will be confirmed that by using the data obtained from the chronic kidney disease patients as a positive control, the result obtained in the present Example is not resulting from diabetes.
(2) Sample Preparation
(2-1) Plasma Sample A methanol solution (450 µL) containing both of L-methioninesulfone and D-camphor-10-sulfonic acid at a final concentration of 10 µM each as internal standards was stirred with 50 µL of plasma. Chloroform (500 µM) and 200 µL of distilled water were stirred therein followed by centrifugation (2,300×g, 4° C., 5 min). The aqueous phase was transferred to ultrafiltration tubes (Ultrafree-MC PBCC centrifugal filter unit 5 kDa: MILLIPORE) (200 µL×2 tubes) and subjected to ultrafiltration (9,100×g, 4° C., 120 min). The filtrate was evaporated to dryness and dissolved in 25 µL of distilled water to obtain plasma samples. The samples were diluted two-fold and used in the measurement described hereinbelow.
(2-2) Urine Sample Distilled water (80 µL) containing the above internal standards at a final concentration of 250 µM each was stirred with 20 μL of urine, transferred to an ultrafiltration tube (Ultrafree-MC PBCC centrifugal filter unit 5 kDa: MILLIPORE) and subjected to ultrafiltration (9,100×g, 4° C., 60 min). The filtrate was evaporated to dryness and dissolved in 25 μL of distilled water to obtain a urine sample. The sample was diluted ten-fold and five-fold, respectively, and used in the cation measurement and anion measurement described hereinbelow.

(3) CE-MS Analysis

The instrument used was Agilent CE-TOF/MS system (Agilent Technologies) and the capillary used was a Fused silica capillary i.d. 50 μm×80 cm.

The measurement conditions were as follows.
CE voltage: cation; 27 kV, anion; 30 kV
MS ionization: ESI Positive or Negative
MS capillary voltage: cation; 4,000 V, anion; 3,500 V
MS scan range: m/z 50-1,000
Sample injection: cation; 50 mbar, 10 sec, anion; 50 mbar, 25 sec.

(4) Identification of Substances

Substances were identified by following procedures.

Figure 2:
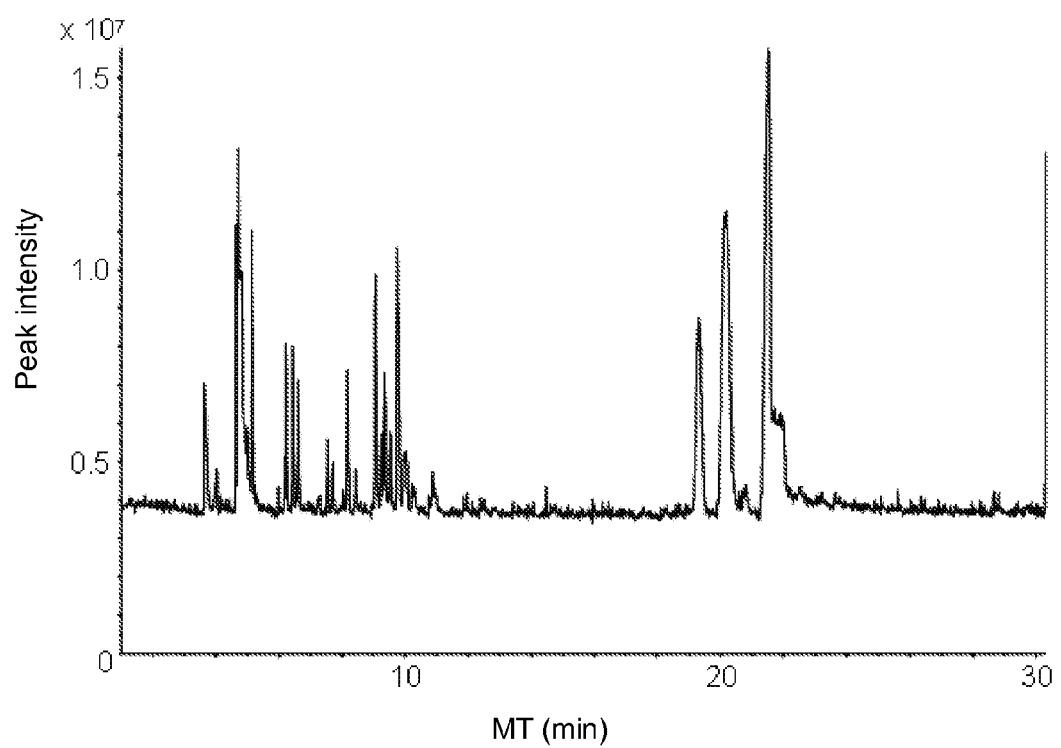
FIG. 2 shows an example of a chart obtained by separating a group of substances by capillary electrophoresis (CE)
Figure 3:
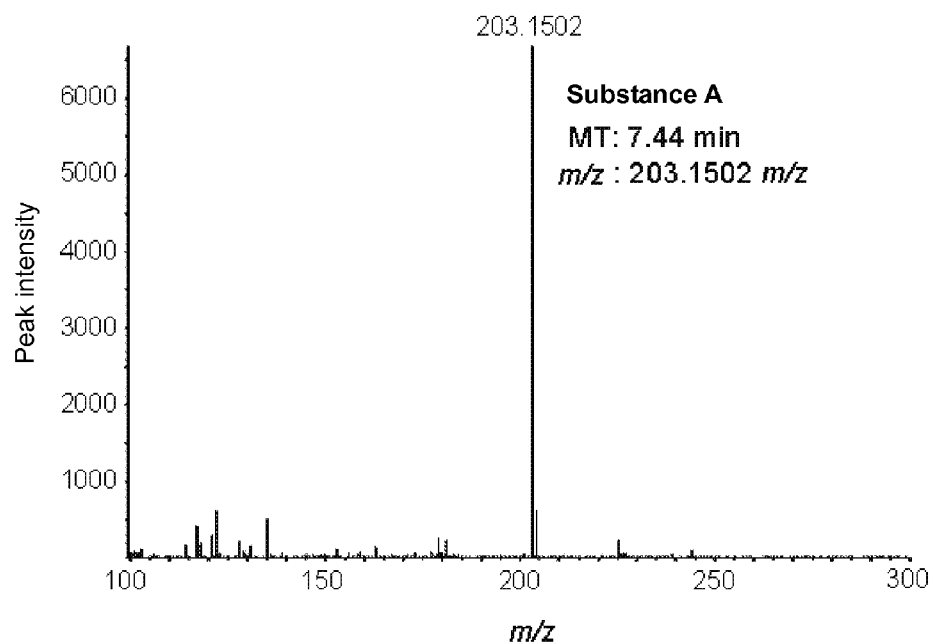
FIG. 3 shows an example of a chart obtained by subjecting the substances separated by CE to mass spectrometry (MS) analysis.

The groups of substances were separated by CE according to ion strength (see FIG. 2) and continuously measured by MS (see FIG. 3). Information on the migration time (min) on CE (hereinafter also abbreviated as "MT") and mass-to-charge ratio (m/z) (calculated to 4 places of decimals; hereinafter also abbreviated as "m/z") of each substance was obtained. The mass-to-charge ratio of the substance of interest was used for calculation of accurate mass. The accurate mass of the substance of interest was then used for search among substances having estimated chemical structures (standard substance) followed by CE-MS analysis of the standard substance.

Figure 4:
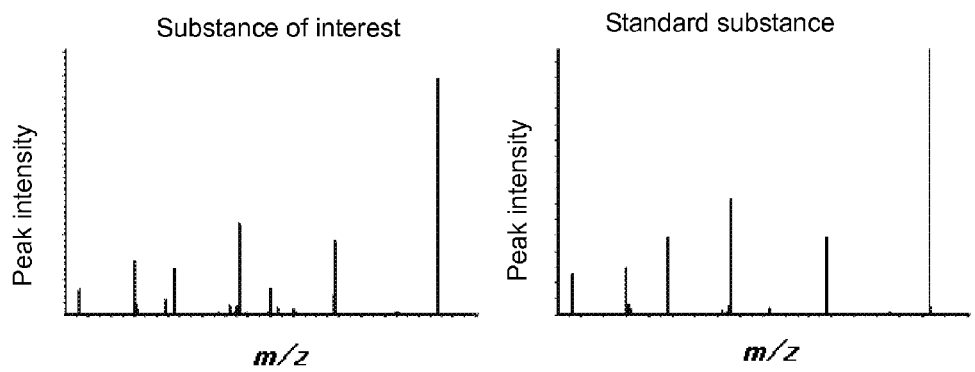
FIG. 4 shows an example of charts obtained from MS/MS analysis of a substance of interest and a standard substance.

In order to obtain substructural information (product ion), the standard substance was subjected to MS/MS analysis (see FIG. 4). The substance of interest and the standard substance were compared for their MT, m/z and MS/MS data. When all data matched, the substance of interest was identified as the standard substance. Tha values of MT and m/z of the identified substances are shown in Table 5.

TABLE 5

| Marker candidates | MT (min) | m/z |
|---|---|---|
| Glycolic acid | 12.78 | 75.0090 |
| $N^5$-[(Dimethylamino)iminomethyl]-ornithine | 7.44 | 203.1502 |
| 5-Oxo-2-tetrahydrofuran carboxylic acid | 10.26 | 129.0198 |
| Trimethylglycine | 10.64 | 118.0859 |
| Guanidinoacetic acid | 7.95 | 118.0610 |
| 4-Guanidinobutyric acid | 8.00 | 146.0922 |
| 2-Oxoglutaric acid | 22.50 | 145.0143 |
| $N^6$-Acetyllysine | 10.78 | 189.1224 |
| $N^1$-Acetylhistidine | 9.37 | 198.0867 |
| Histidine | 7.08 | 156.0764 |
| Glycocyamidine | 6.60 | 100.0502 |
| Cytidine | 9.26 | 244.1091 |
| Valine | 9.56 | 118.0858 |
| Kynurenine | 8.65 | 209.0914 |
| Choline | 6.01 | 104.1068 |
| Cystine | 10.40 | 241.0302 |
| Tryptophan | 9.56 | 205.0968 |
| Ornithine | 5.98 | 133.0973 |
| Glycine | 8.03 | 76.0395 |
| Methionine | 10.18 | 150.0584 |

(5) Criteria for Selection of Marker Candidates

The substances whose concentration or concentration ratio in respective pathological conditions of kidney disease follow any of variation patterns shown in FIG. 1 according to the analysis results of the samples by CE-MS were chosen as marker candidates.

(6) Selection Results of Marker Candidates

Figure 5:
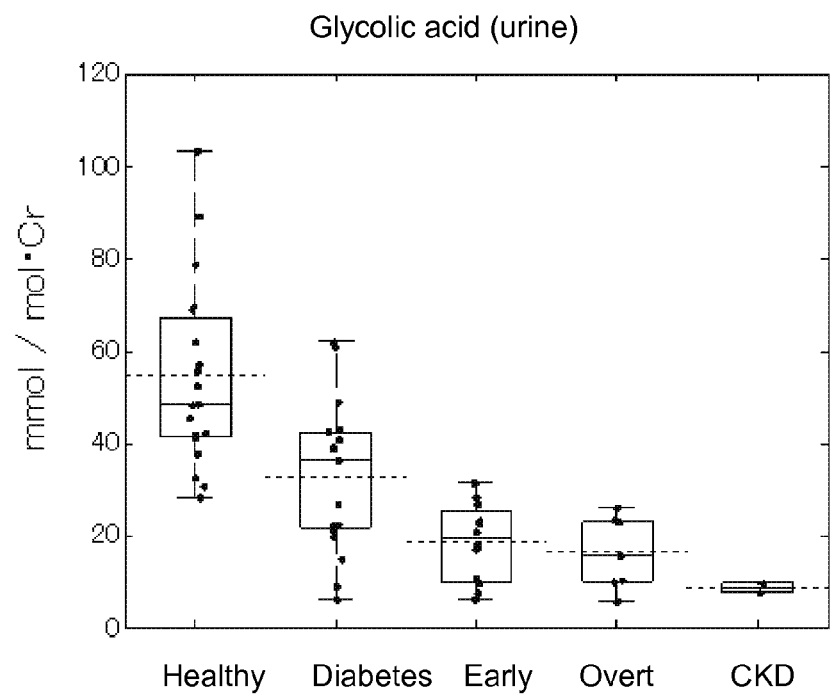
FIG. 5 is a representation of quantitative values of glycolic acid in urine in the groups of healthy subjects and respective patients.
Figure 6:
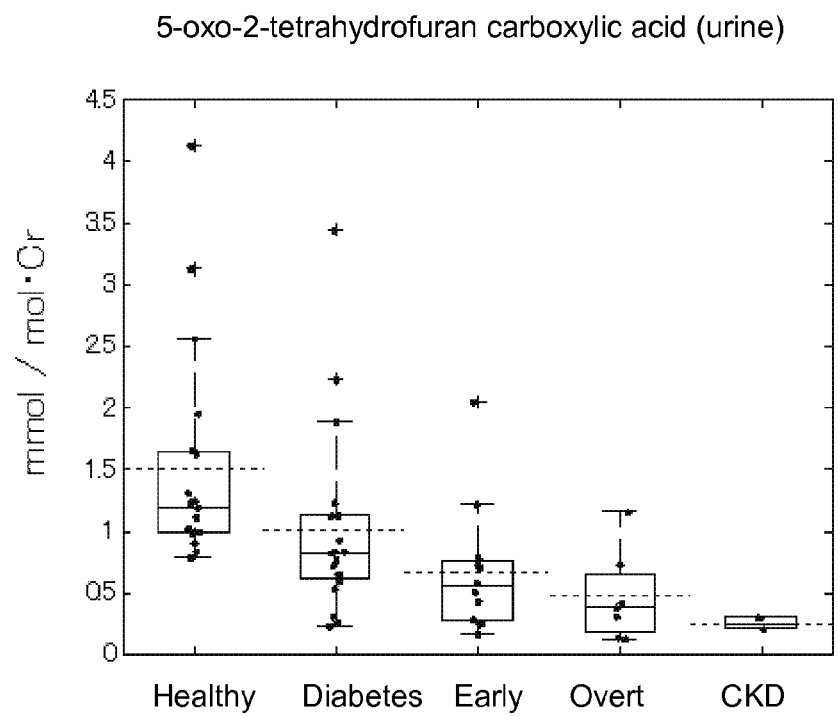
FIG. 6 is a representation of quantitative values of 5-oxo-2-tetrahydrofuran carboxylic acid in urine in the groups of healthy subjects and respective patients.
Figure 7A:
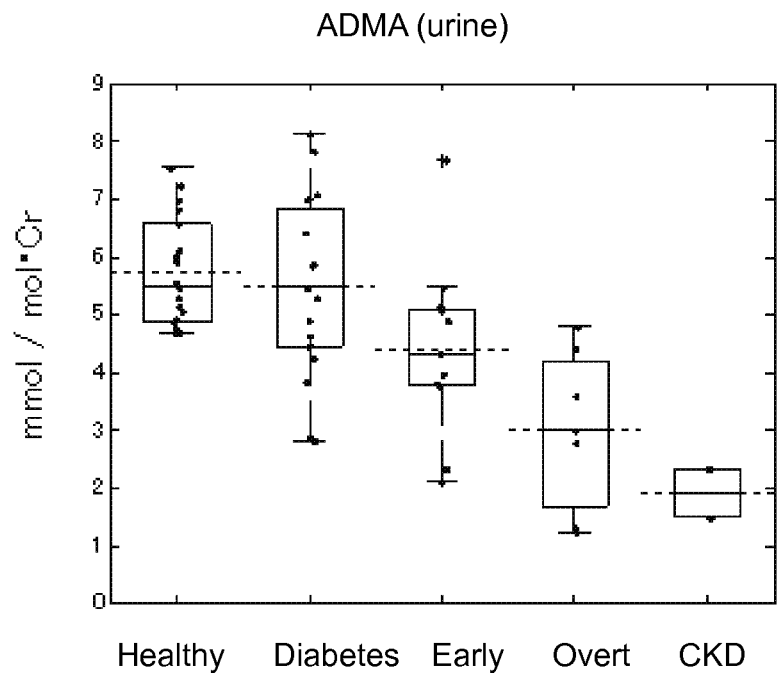
FIG. 7A-7C show representations of quantitative values of $N^5$-[(dimethylamino)iminomethyl]-ornithine (hereinafter also referred to as "ADMA") in the groups of healthy subjects and respective patients.
Figure 7B:
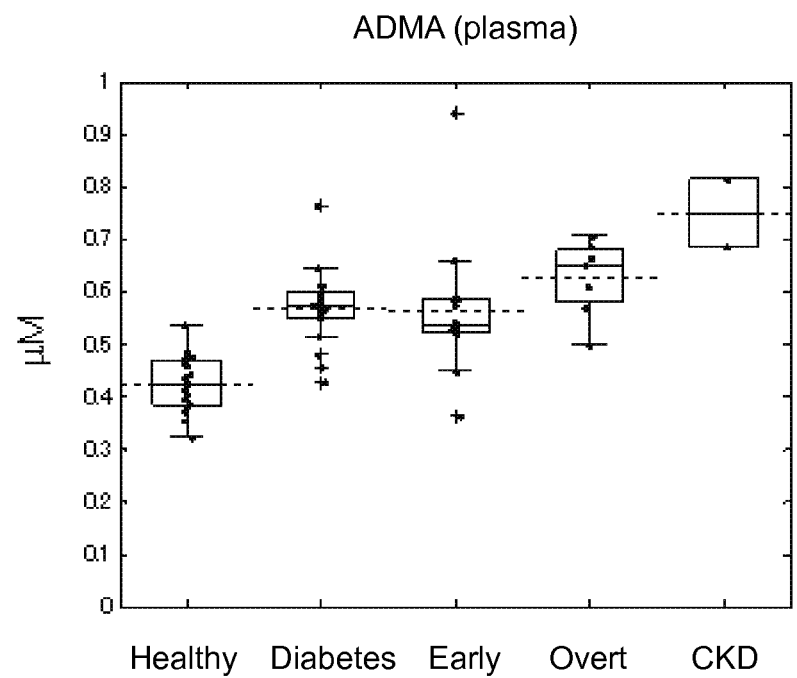
Figure 7C:
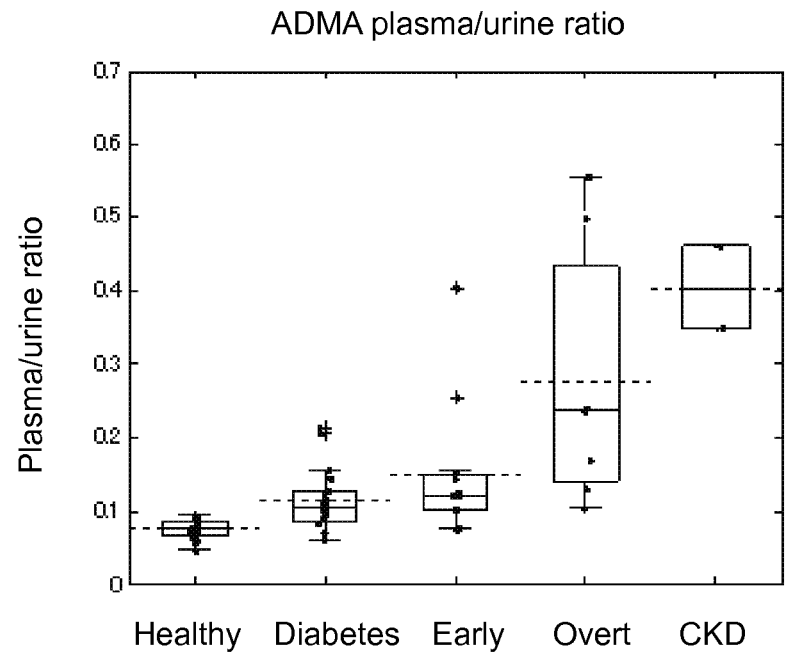
Figure 8:
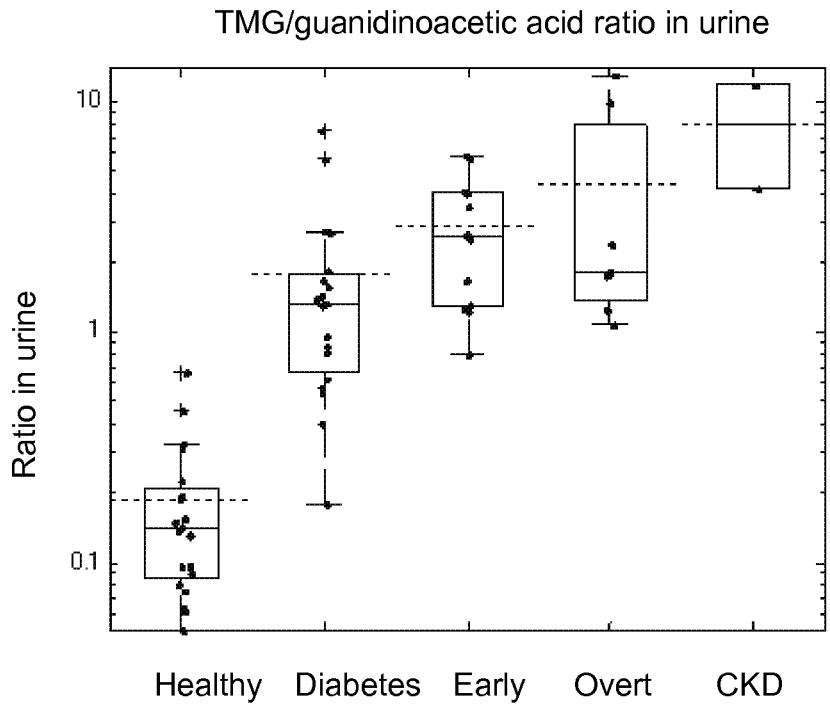
FIG. 8 is a representation of the ratios between trimethylglycine (hereinafter also referred to as "TMG") in urine and guanidinoacetic acid in urine in the groups of healthy subjects and respective patients.
Figure 9:
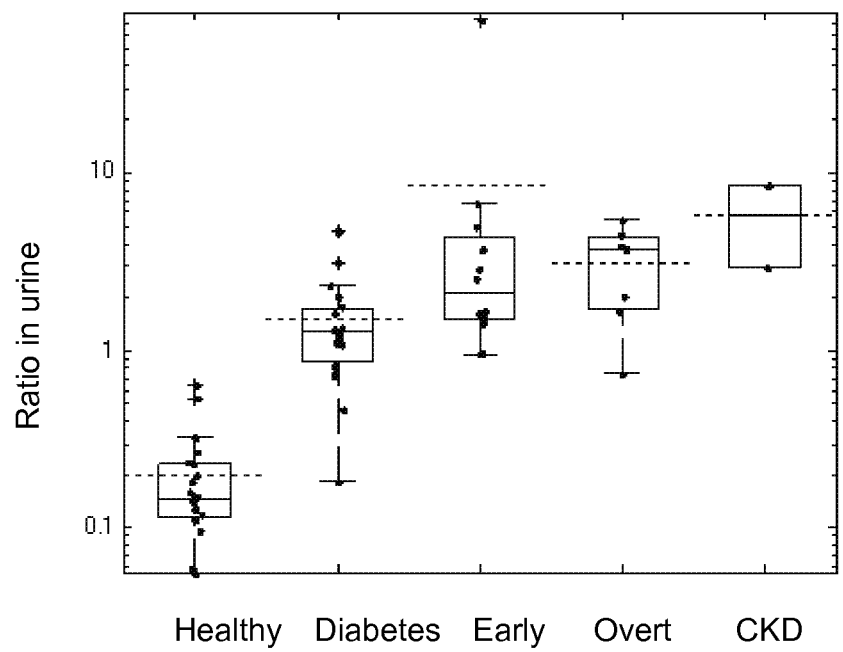
FIG. 9 is a representation of the ratios between TMG in urine and glycolic acid in urine in the groups of healthy subjects and respective patients.
Figure 10:
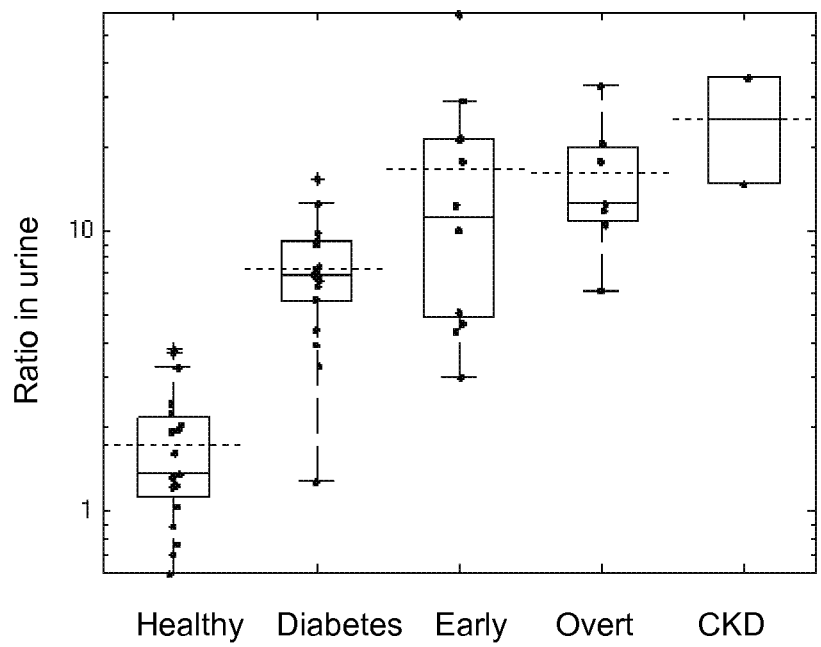
FIG. 10 is a representation of the ratios between TMG in urine and ADMA in urine in the groups of healthy subjects and respective patients.
Figure 11:
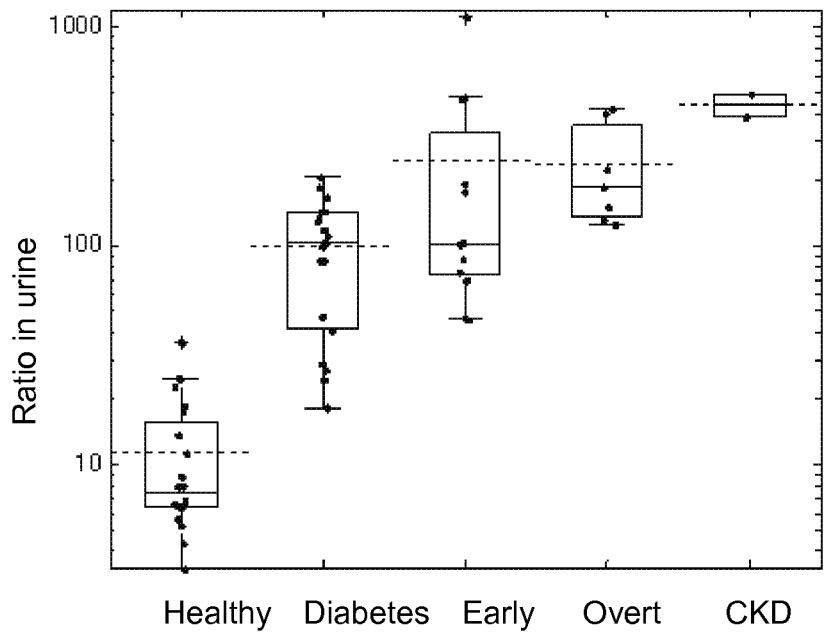
FIG. 11 is a representation of the ratios between TMG in urine and 4-guanidinobutyric acid in urine in the groups of healthy subjects and respective patients.
Figure 12:
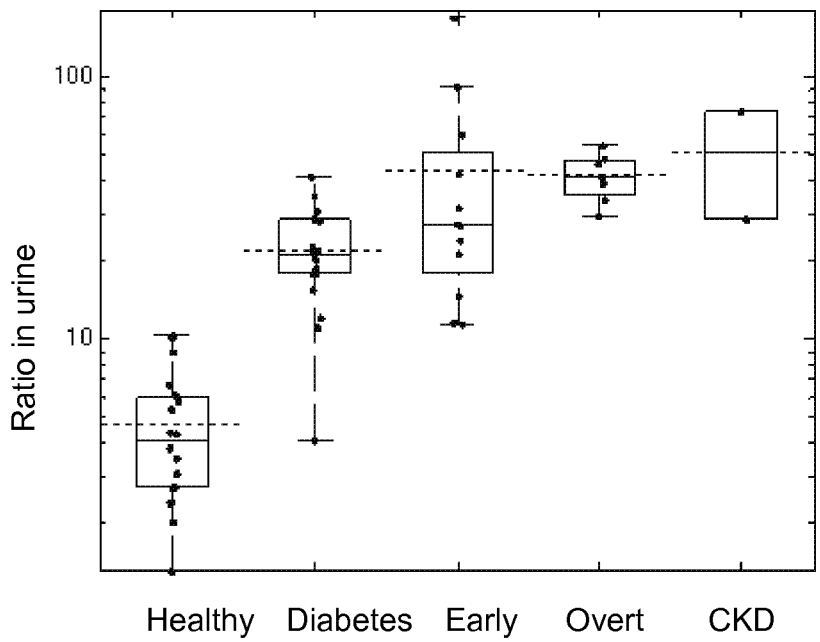
FIG. 12 is a representation of the ratios between TMG in urine and $N^6$-acetyllysine in urine in the groups of healthy subjects and respective patients.
Figure 13:
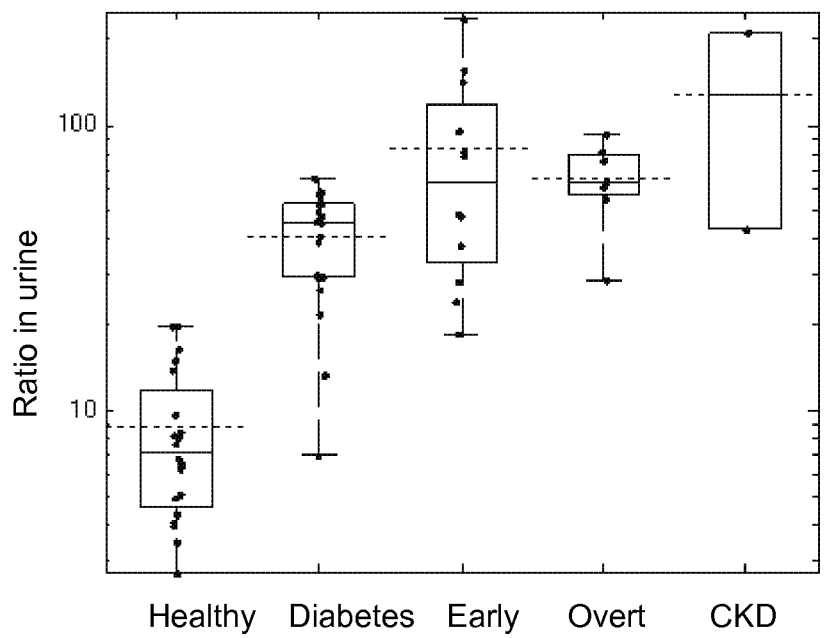
FIG. 13 is a representation of the ratios between TMG in urine and $N^1$-acetylhistidine in urine in the groups of healthy subjects and respective patients.
Figure 14:
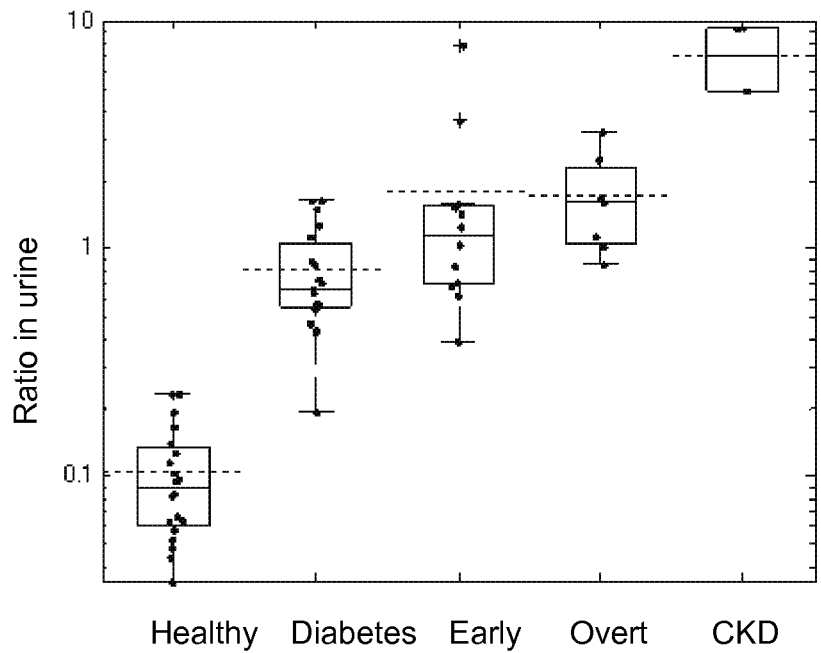
FIG. 14 is a representation of the ratios between TMG in urine and histidine in urine in the groups of healthy subjects and respective patients.
Figure 15:
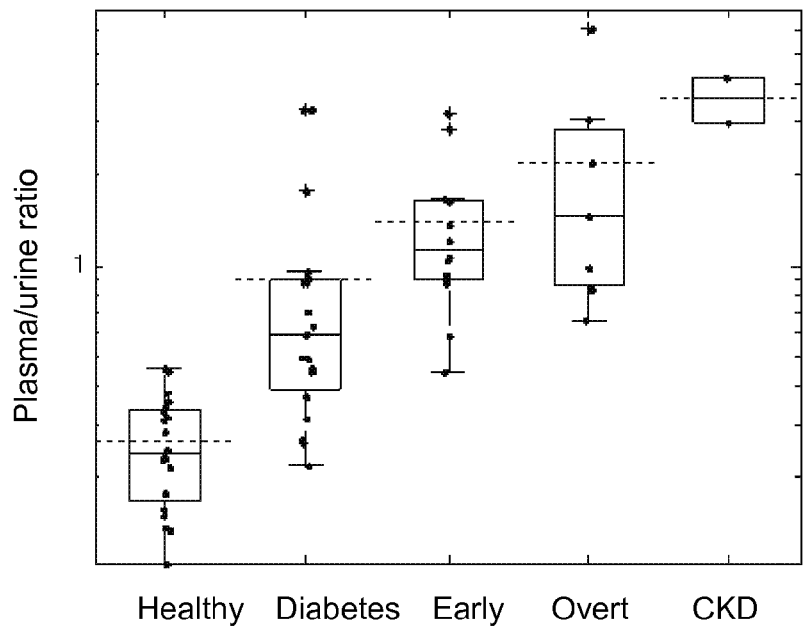
FIG. 15 is a representation of the ratios between choline in plasma and glycolic acid in urine in the groups of healthy subjects and respective patients.
Figure 16:
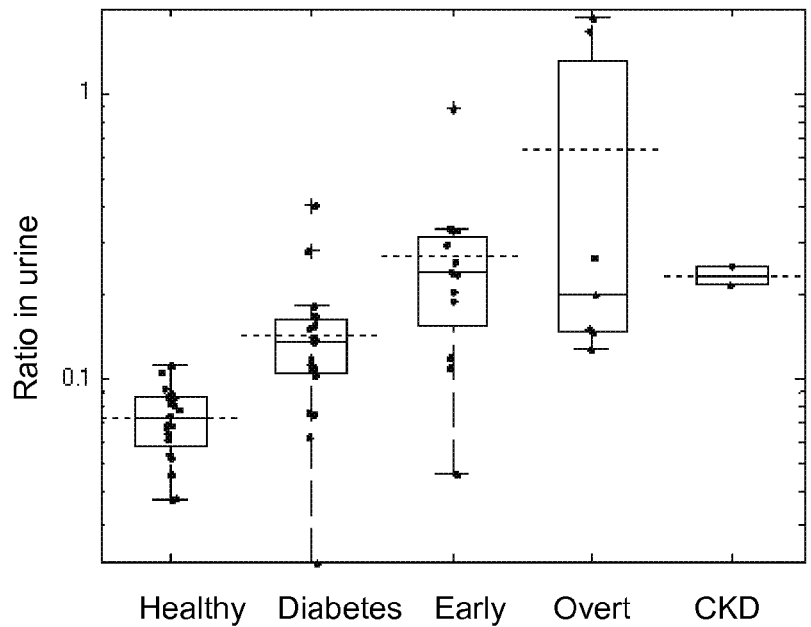
FIG. 16 is a representation of the ratios between valine in urine and glycolic acid in urine in the groups of healthy subjects and respective patients.
Figure 17:
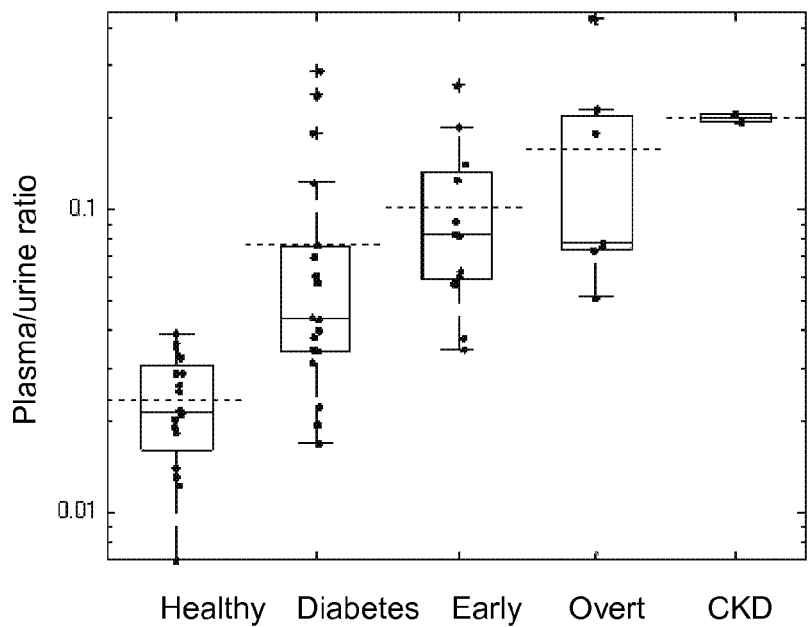
FIG. 17 is a representation of the ratios between kynurenine in plasma and glycolic acid in urine in the groups of healthy subjects and respective patients.
Figure 18:
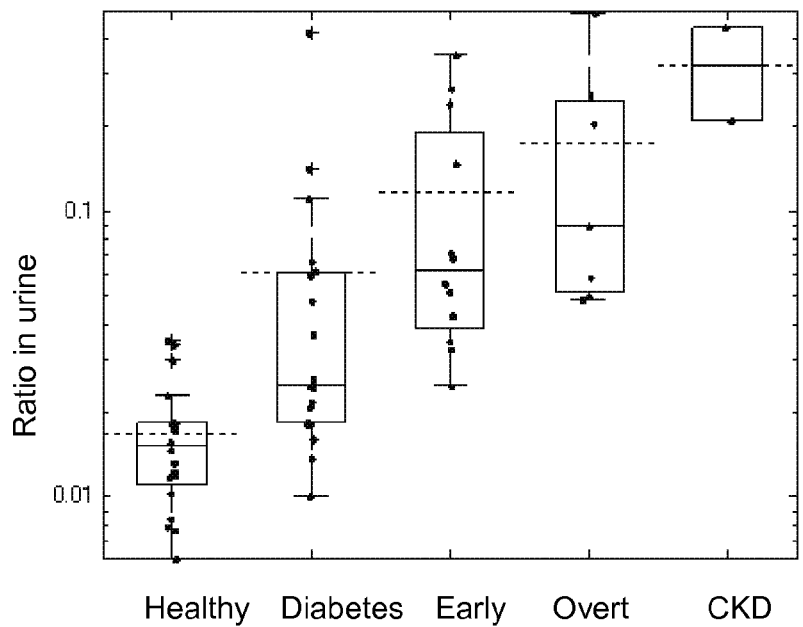
FIG. 18 is a representation of the ratios between glycocyamidine in urine and glycolic acid in urine in the groups of healthy subjects and respective patients.
Figure 19:
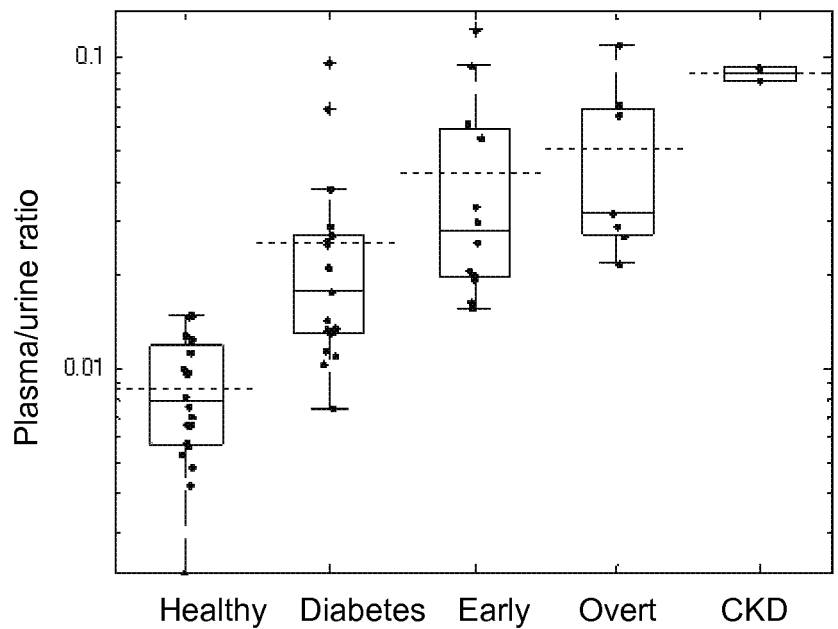
FIG. 19 is a representation of the ratios between ADMA in plasma and glycolic acid in urine in the groups of healthy subjects and respective patients.
Figure 20:
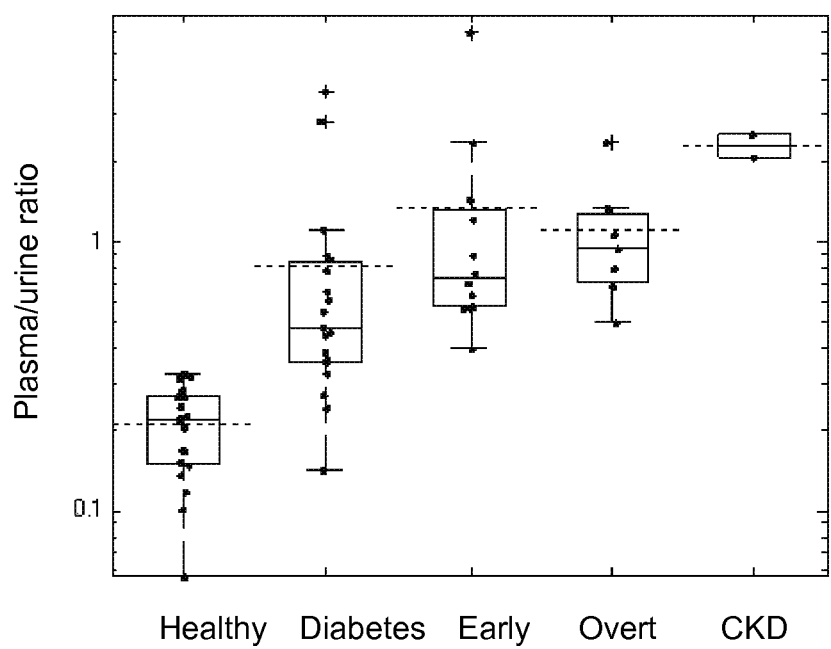
FIG. 20 is a representation of the ratios between 2-oxoglutaric acid in plasma and glycolic acid in urine in the groups of healthy subjects and respective patients.
Figure 21:
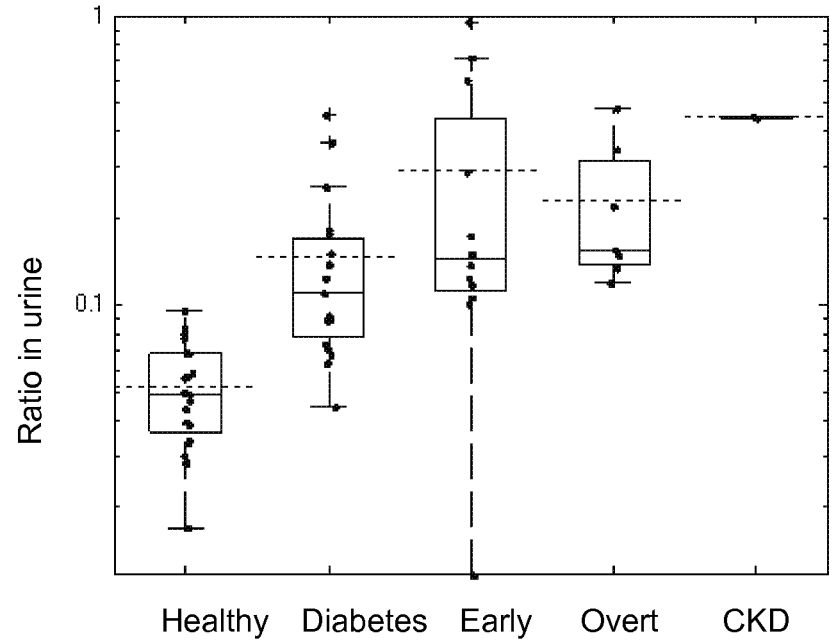
FIG. 21 is a representation of the ratios between cytidine in urine and glycolic acid in urine in the groups of healthy subjects and respective patients.
Figure 22:
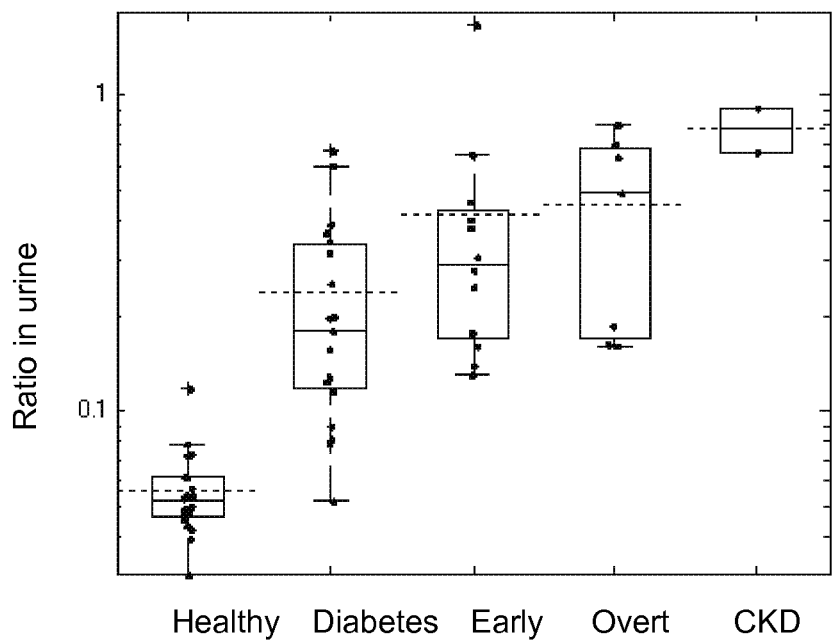
FIG. 22 is a representation of the ratios between cystine in urine and histidine in urine in the groups of healthy subjects and respective patients.
Figure 23:
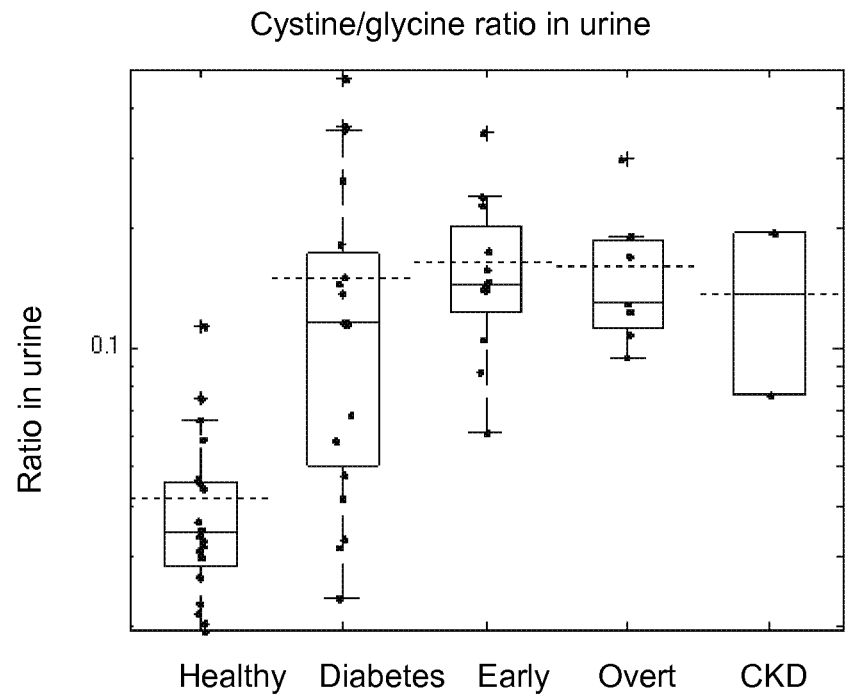
FIG. 23 is a representation of the ratios between cystine in urine and glycine in urine in the groups of healthy subjects and respective patients.
Figure 24:
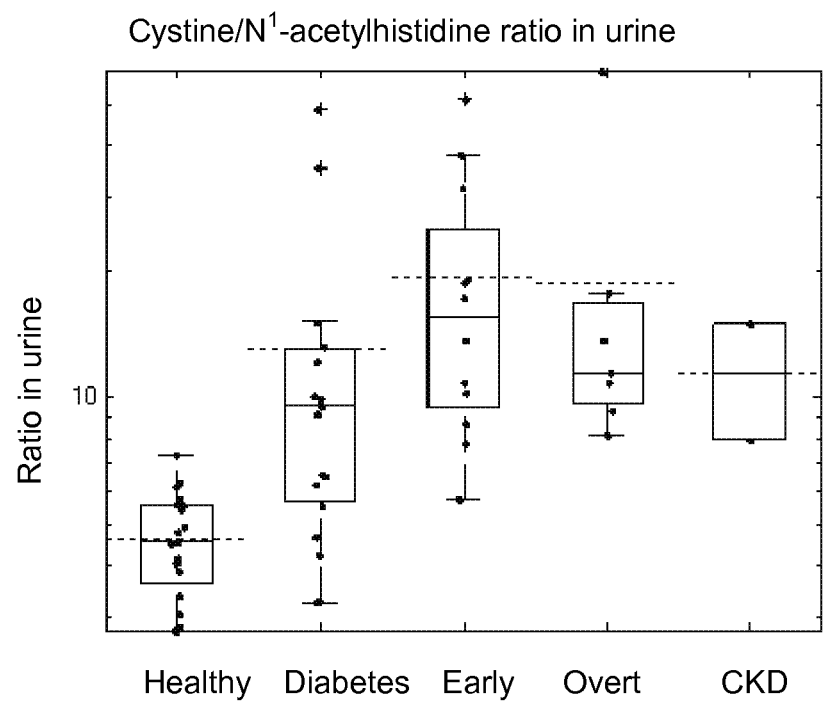
FIG. 24 is a representation of the ratios between cystine in urine and $N^1$-acetylhistidine in urine in the groups of healthy subjects and respective patients.
Figure 25:
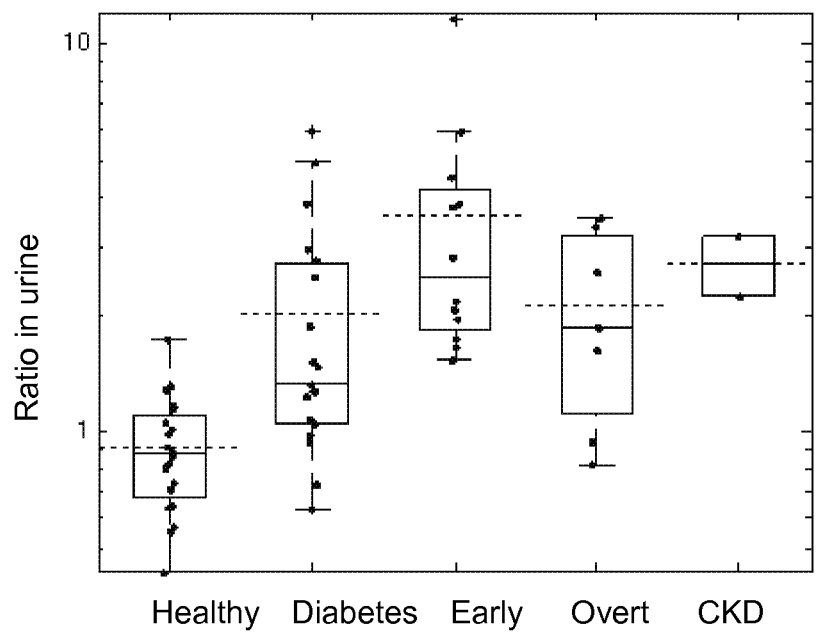
FIG. 25 is a representation of the ratios between cystine in urine and tryptophan in urine in the groups of healthy subjects and respective patients.
Figure 26:
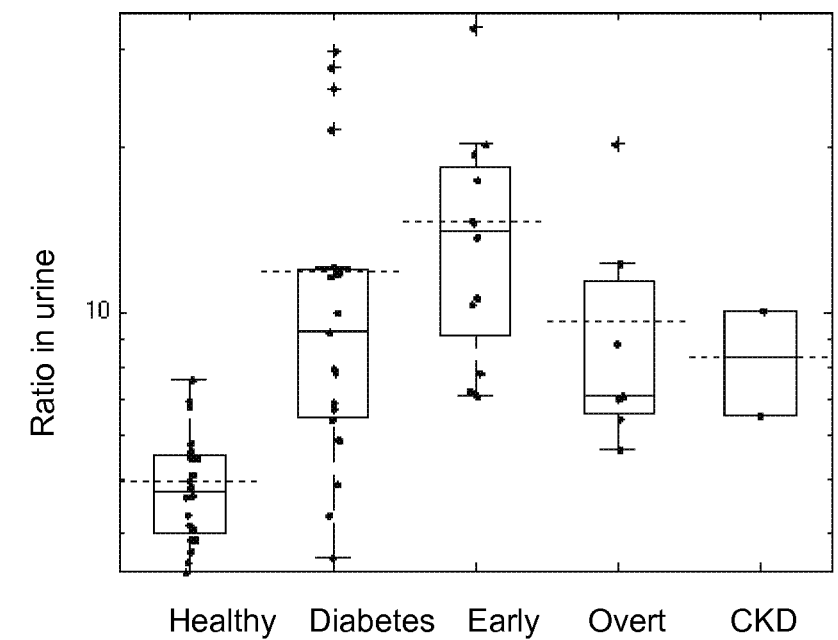
FIG. 26 is a representation of the ratios between cystine in urine and methionine in urine in the groups of healthy subjects and respective patients.
Figure 27:
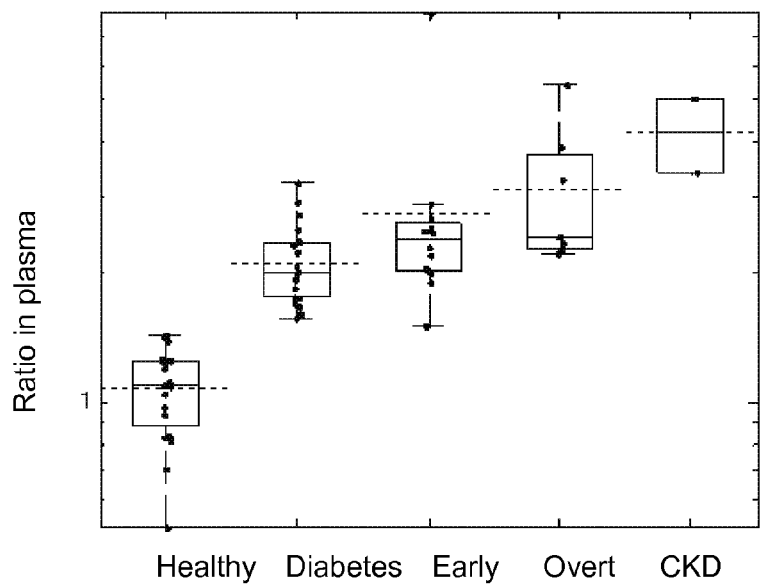
FIG. 27 is a representation of the ratios between ornithine in plasma and tryptophan in plasma in the groups of healthy subjects and respective patients.

The number of MS peaks obtained by CE-MS analysis as described in the above (3) was 700 and 902 for plasma and urine samples, respectively. The relative peak area values were obtained for those peaks by correction with the internal standards for plasma samples and with the internal standards and urenal creatinine for urine samples and were used for selection of marker candidates. The results are shown in FIGS. 5 to 7. The substances which may be used as a marker by itself are shown in Table 6.

TABLE 6

| Variation pattern | Substance which can be a merker by itself |
|---|---|
| FIG. 1C | Glycolic acid (urine) |
| | 5-Oxo-2-tetrahydrofuran carboxylic acid (urine) |
| FIG. 1A | $N^5$-[(dimethylamino)iminomethyl]-ornithine (plasma/urine) |

The measurement value for glycolic acid or 5-oxo-2-tetrahydrofuran carboxylic acid in urine follows the variation pattern in which it decreases from "Healthy" to "Early" as shown in FIG. 1C.

Thus, it was found that the value of the concentration of glycolic acid or 5-oxo-2-tetrahydrofuran carboxylic acid in urine obtained from a subject can be used to determine whether or not the subject has kidney disease.

The ratio of ADMA between in urine and plasma shows the tendency in which it increased from "Healthy" to "Early" as shown in FIG. 1A.

Thus, it was found that the value of "the concentration in plasma/the concentration in urine" in urine and plasma obtained from a subject can be used to determine whether or not the subject has kidney disease.

Example 2

From the substances identified in Example 1, the substances were selected which may serve as a marker in combination. The concentration in combination of the substances in urine and plasma from healthy subjects and kidney disease patients in respective pathological conditions were examined.

Marker candidates in the combination of two substances were chosen when the ratio obtained by dividing the concentration of one substance by the concentration of the other substance follows the variation patterns of the concentration ratio in respective pathological conditions of kidney disease as shown in FIG. 1.

The results are shown in FIGS. 8 to 27. The relations between the value relating to the concentration ratio of the marker consisting of a combination of two substances and the variation pattern of the value relating to the concentration ratio in respective pathological conditions of kidney disease are shown in Tables 7 to 10.

TABLE 7

| Substance A | Substance B | Value relating to concentration ratio | Variation pattern |
|---|---|---|---|
| TMG | Glycolic acid | A (urine)/B (urine) | FIG. 1B |
| TMG | ADMA | A (urine)/B (urine) | FIG. 1B |
| TMG | Guanidinoacetic acid | A (urine)/B (urine) | FIG. 1A |

TABLE 7-continued

| Substance A | Substance B | Value relating to concentration ratio | Variation pattern |
|---|---|---|---|
| TMG | 4-Guanidinobutyric acid | A (urine)/B (urine) | FIG. 1B |
| TMG | N⁶-Acetyllysine | A (urine)/B (urine) | FIG. 1B |
| TMG | N¹-Acetylhistidine | A (urine)/B (urine) | FIG. 1B |
| TMG | Histidine | A (urine)/B (urine) | FIG. 1B |

All of the values (A (urine)/B (urine)) obtained by dividing the value of the concentration of trimethylglycine (substance A) in urine by the value of the concentration of substance B in urine for the combinations of two substances (substances A and B) shown in Table 7 show the tendency that they increase from "Healthy" to "Early" as shown in FIG. 1A or 1B.

Thus, it was found that the value of A (urine)/B (urine) of two substances shown in Table 7 in urine obtained from a subject can be used to determine whether or not the subject has kidney disease.

TABLE 8

| Substance A | Substance B | Value relating to concentration ratio | Variation pattern |
|---|---|---|---|
| Glycolic acid | ADMA | B (plasma)/A (urine) | FIG. 1B |
| Glycolic acid | Cytidine | B (urine)/A (urine) | FIG. 1B |
| Glycolic acid | Valine | B (urine)/A (urine) | FIG. 1A |
| Glycolic acid | Kynurenine | B (plasma)/A (urine) | FIG. 1A |
| Glycolic acid | 2-oxoglutaric acid | B (plasma)/A (urine) | FIG. 1B |
| Glycolic acid | Glycocyamidine | B (urine)/A (urine) | FIG. 1A |
| Glycolic acid | Choline | B (plasma)/A (urine) | FIG. 1A |

All of the values (B (plasma)/A (urine) or B (urine)/A (urine)) obtained by dividing the value of the concentration of the substance in plasma or urine by the value of the concentration of glycolic acid (substance A) in urine for the combinations of two substances shown in Table 8 show the tendency that they increase from "Healthy" to "Early" as shown in FIG. 1A or 1B.

Thus, it was found that the value of B (plasma)/A (urine) or B (urine)/A (urine) of two substances shown in Table 8 in urine and plasma obtained from a subject can be used to determine whether or not the subject has kidney disease.

TABLE 9

| Substance A | Substance B | Value relating to concentration ratio | Variation pattern |
|---|---|---|---|
| Cystine | N¹-Acetylhistidine | A (urine)/B (urine) | FIG. 1B |
| Cystine | Histidine | A (urine)/B (urine) | FIG. 1B |
| Cystine | Glycine | A (urine)/B (urine) | FIG. 1B |
| Cystine | Tryptophan | A (urine)/B (urine) | FIG. 1B |
| Cystine | Methionine | A (urine)/B (urine) | FIG. 1B |

All of the values (A (urine)/B (urine)) obtained by dividing the value of the concentration of cystine (substance A) in urine by the value of the concentration of the substance B in urine show the tendency that they increase from "Healthy" to "Early" as shown in FIG. 1B.

Thus, it was found that the value of A (urine)/B (urine) of two substances shown in Table 9 in urine obtained from a subject can be used to determine whether or not the subject has kidney disease.

TABLE 10

| Substance A | Substance B | Value relating to concentration ratio | Variation pattern |
|---|---|---|---|
| Tryptophan | Ornithine | B (plasma)/A (plasma) | FIG. 1A |

The value (B (plasma)/A (plasma)) obtained by dividing the value of the concentration of ornithine (substance B) in plasma by the value of the concentration of tryptophan (substance A) in plasma for the combination of two substances shown in Table 10 shows the tendency that it increases from "Healthy" to "Early" as shown in FIG. 1A.

Thus, it was found that the value of B (plasma)/A (plasma) of two substances shown in Table 10 in plasma obtained from a subject can be used to determine whether or not the subject has kidney disease.

DESCRIPTION OF THE REFERENCE NUMERALS

100 Computer
110 Main unit
110a CPU
110b ROM
110c RAM
110d Hard disk
110e Read-out system
110f Input-output interface
110g Image output interface
110h Bus
120 Display unit
130 Input-output device
140 Portable memory medium
140a Computer program
200 Measurement apparatus

What is claimed is:

1. A method for diagnosing kidney disease in a patient, comprising the steps of:
   (1) obtaining a sample from a patient suspected of having kidney disease;
   (2) analyzing said sample to determine the concentration of trimethylglycine and guanidinoacetic acid in said sample; and dividing the trimethylglycine concentration in said sample by the guanidinoacetic acid concentration in said sample to produce a first ratio value, or dividing the guanidinoacetic acid concentration in said sample by the trimethylglycine concentration in said sample to produce a second ratio value; and
   (3) recording a diagnosis that said patient has kidney disease when said first ratio value is elevated or said second ratio value is lowered in comparison to healthy persons 2. The method according to claim 1, wherein the kidney disease is diabetic nephropathy.

3. The method according to claim 1, wherein said sample is selected from the group consisting of plasma and urine.

4. The method according to claim 3, wherein said sample is urine.

* * * * *